United States Patent
Buelna et al.

(10) Patent No.: US 12,310,927 B2
(45) Date of Patent: May 27, 2025

(54) METHODS AND SYSTEMS FOR ABLATION OF THE RENAL PELVIS

(71) Applicant: Verve Medical, Inc., Paradise Valley, AZ (US)

(72) Inventors: Terrence J. Buelna, Santa Barbara, CA (US); Adam Gold, Glendale, AZ (US); Rahul Rao, Phoenix, AZ (US)

(73) Assignee: Verve Medical, Inc., Peoria, IL (US)

( * ) Notice: Subject to any disclaimer, the term of this patent is extended or adjusted under 35 U.S.C. 154(b) by 0 days.

(21) Appl. No.: 17/097,387

(22) Filed: Nov. 13, 2020

(65) Prior Publication Data

US 2021/0077419 A1  Mar. 18, 2021

Related U.S. Application Data

(62) Division of application No. 14/616,576, filed on Feb. 6, 2015, now abandoned.
(Continued)

(51) Int. Cl.
*A61K 31/045* (2006.01)
*A61B 17/32* (2006.01)
(Continued)

(52) U.S. Cl.
CPC ........ *A61K 31/045* (2013.01); *A61B 18/1492* (2013.01); *A61B 2017/320008* (2013.01);
(Continued)

(58) Field of Classification Search
CPC .... A61B 2018/0016; A61B 2018/0214; A61B 218/00511; A61B 2018/1407; A61B 2018/1435; A61B 2018/1417; A61B 2018/00404; A61B 2018/1467; A61B 2018/1475
See application file for complete search history.

(56) References Cited

U.S. PATENT DOCUMENTS

| 8,548,600 B2 | 10/2013 | Deem et al. |
| 9,668,811 B2 | 6/2017 | Sogard et al. |

(Continued)

FOREIGN PATENT DOCUMENTS

| JP | 2013544133 A | 12/2013 |
| WO | WO-9744088 A1 | 11/1997 |

(Continued)

OTHER PUBLICATIONS

Extended European Search Report dated Sep. 28, 2017 for European Patent Application No. EP15746617.8.
(Continued)

*Primary Examiner* — Ronald Hupczey, Jr.

(57) ABSTRACT

Apparatus, systems, and methods provide access to the renal pelvis of a kidney to treat renal nerves embedded in tissue surrounding the renal pelvis. Access to the renal pelvis may be via the urinary tract or via minimally invasive incisions through the abdomen and kidney tissue. Treatment is effected by exchanging energy, typically delivering heat or extracting heat through a wall of the renal pelvis, or by delivering active substances to ablate a thin layer of tissue lining at least a portion of the renal pelvis to disrupt renal nerves within the tissue lining of the renal pelvis.

6 Claims, 35 Drawing Sheets

Related U.S. Application Data

(60) Provisional application No. 62/074,894, filed on Nov. 4, 2014, provisional application No. 62/003,918, filed on May 28, 2014, provisional application No. 61/937,353, filed on Feb. 7, 2014.

(51) Int. Cl.
*A61B 18/00* (2006.01)
*A61B 18/04* (2006.01)
*A61B 18/14* (2006.01)
*A61B 18/18* (2006.01)
*A61N 1/32* (2006.01)
*A61N 7/02* (2006.01)

(52) U.S. Cl.
CPC .......... *A61B 2017/320069* (2017.08); *A61B 2018/00214* (2013.01); *A61B 2018/0022* (2013.01); *A61B 2018/00267* (2013.01); *A61B 2018/00434* (2013.01); *A61B 2018/00511* (2013.01); *A61B 2018/00577* (2013.01); *A61B 2018/00797* (2013.01); *A61B 2018/00821* (2013.01); *A61B 2018/044* (2013.01); *A61B 2018/1417* (2013.01); *A61B 2018/1435* (2013.01); *A61B 2018/1861* (2013.01); *A61N 1/325* (2013.01); *A61N 7/022* (2013.01)

(56) References Cited

U.S. PATENT DOCUMENTS

| | | | |
|---|---|---|---|
| 10,357,302 | B2 | 7/2019 | Buelna et al. |
| 2003/0153905 | A1 | 8/2003 | Edwards et al. |
| 2009/0024195 | A1 | 1/2009 | Rezai et al. |
| 2011/0060324 | A1 | 3/2011 | Wu et al. |
| 2011/0104061 | A1 | 5/2011 | Seward et al. |
| 2011/0301662 | A1 | 12/2011 | Bar-Yoseph et al. |
| 2012/0029513 | A1 | 2/2012 | Smith et al. |
| 2012/0078160 | A1 | 3/2012 | Mcmillan |
| 2012/0101538 | A1 | 4/2012 | Ballakur et al. |
| 2012/0116382 | A1* | 5/2012 | Ku ............ A61M 25/0138 606/33 |
| 2012/0123303 | A1 | 5/2012 | Sogard et al. |
| 2012/0130368 | A1* | 5/2012 | Jenson ............ A61B 18/1492 606/41 |
| 2013/0053732 | A1 | 2/2013 | Heuser et al. |
| 2013/0165926 | A1 | 6/2013 | Mathur et al. |
| 2013/0178824 | A1 | 7/2013 | Buelna |
| 2014/0107639 | A1 | 4/2014 | Zhang et al. |
| 2015/0065783 | A1 | 3/2015 | Buelna |
| 2015/0223866 | A1 | 8/2015 | Buelna et al. |
| 2015/0342531 | A1 | 12/2015 | Hoitink et al. |
| 2019/0329042 | A1 | 10/2019 | DiLorenzo |

FOREIGN PATENT DOCUMENTS

| | | | | |
|---|---|---|---|---|
| WO | WO-2005000130 | A1 * | 1/2005 | ....... A61B 17/22031 |
| WO | WO-2010067360 | A2 | 6/2010 | |
| WO | WO-2012061161 | A1 | 5/2012 | |
| WO | WO-2012170482 | A1 | 12/2012 | |
| WO | WO-2013010009 | A1 * | 1/2013 | ............. A61B 18/00 |
| WO | WO-2013134469 | A1 * | 9/2013 | ............. A61B 18/02 |
| WO | WO-2015120340 | A1 | 8/2015 | |

OTHER PUBLICATIONS

"International search report and written opinion dated Jul. 10, 2015 for PCT/US2015/014926.".
"Office action dated Jan. 26, 2018 for U.S. Appl. No. 14/616,576.".
Office action dated Feb. 26, 2019 for U.S. Appl. No. 14/616,576.
Office action dated May 19, 2020 for U.S. Appl. No. 14/616,576.
Office Action dated Jun. 13, 2017 for U.S. Appl. No. 14/616,576.
Office action dated Nov. 13, 2019 for U.S. Appl. No. 14/616,576.
Non-Final Office Action dated Dec. 29, 2023 from U.S. Appl. No. 17/143,725.
Non-Final Office Action dated Apr. 9, 2024 from U.S. Appl. No. 18/412,229.
Non-Final Office Action dated Apr. 25, 2024 from U.S. Appl. No. 18/412,240.
Non-Final Office Action dated Jul. 18, 2024 from U.S. Appl. No. 17/143,725.
Notice of Allowance dated Aug. 7, 2024 from U.S. Appl. No. 18/412,229.
Notice of Allowance dated Aug. 27, 2024 from U.S. Appl. No. 18/412,240.
Kopp, U. C. (2011). Neural control of renal function, Colloquium Series in Integrated Systems Physiology: From Molecule to Function, Morgan & Claypool Life Sciences. (Submitted as Exhibit B to the DiBona Declaration).
Dibona, G. F., & Esler, M. (2010). Translational medicine: the antihypertensive effect of renal denervation. American Journal of Physiology—Regulatory, Integrative and Comparative Physiology, 298(2), R245-R253. (Submitted as Exhibit C to the DiBona Declaration).
Esler, M. (2011). The sympathetic nervous system through the ages: from Thomas Willis to resistant hypertension. Experimental physiology, 96(7), 611-622. (Submitted as Exhibit D to the DiBona Declaration).
Vase, H., Mathiassen, O. N., Kaltoft, A., Pedersen, E. B., Christensen, K. L., Buus, N. H., . . . & Thuesen, L. (2012). Catheter-based renal denervation for treatment of resistant hypertension. Dan Med J, 59(6), A4439. (Submitted as Exhibit E to the DiBona Declaration).
Zhang, Y., Hata, C., & De La Rama, A., U.S. Appl. No. 61/493,849, filed Jun. 6, 2011, entitled "Renal Denervation System and Method," 17 pages. (Submitted as Exhibit F to the DiBona Declaration).
Tunev, S. S., & Trudel, J., File History of U.S. Appl. No. 61/608,022, filed Mar. 7, 2012, entitled "Selective Modulation of Renal Nerves," 58 pages. (Submitted as Exhibit H to the DiBona Declaration).
Mitterberger, M., Pinggera, G. M., Feuchtner, G., Neururer, R., Bartsch, G., Gradl, J., . . . & Frauscher, F. (2007). Sonographic measurement of renal pelvis wall thickness as diagnostic criterion for acute pyelonephritis in adults. Ultraschall in der Medizin—European Journal of Ultrasound, 28(06), 593-597. (Submitted as Exhibit I to the DiBona Declaration).
Weizer, A. Z., Raj, G. V., O'Connell, M., Robertson, C. N., Nelson, R. C., & Polascik, T. J. (2005). Complications after percutaneous radiofrequency ablation of renal tumors. Urology, 66(6), 1176-1180. (Submitted as Exhibit K to the DiBona Declaration).
Gervais, D. A., Arellano, R. S., Mcgovern, F. J., Mcdougal, W. S., & Mueller, P. R. (2005). Radiofrequency ablation of renal cell carcinoma: part 2, Lessons learned with ablation of 100 tumors. American Journal of Roentgenology, 185(1), 72-80. (Submitted as Exhibit M to the DiBona Declaration).
Caliskan, S., & Cevik, R. (2016). Retroperitoneal urinoma after percutaneous nephrolithotomy. Medicine Science, 5 (2), 720-724. (Submitted as Exhibit N to the DiBona Declaration).
Sakakura, K., Ladich, E., Cheng, Q., Otsuka, F., Yahagi, K., Fowler, D. R., . . . & Joner, M. (2014). Anatomic assessment of sympathetic peri-arterial renal nerves in man. Journal of the American College of Cardiology, 64(7), 635-643. (Submitted as Exhibit O to the DiBona Declaration).
Vink, E. E., Goldschmeding, R., Vink, A., Weggemans, C., Bleijs, R. L., & Blankestijn, P. J. (2014). Limited destruction of renal nerves after catheter-based renal denervation: results of a human case study. Nephrology Dialysis Transplantation, 29(8), 1608-1610. (Submitted as Exhibit P to the DiBona Declaration).
Bhatt, D. L., Kandzari, D. E., O'Neill, W. W., D'Agostino, R., Flack, J. M., Katzen, B. T., . . . & Bakris, G. L. (2014). A controlled trial of renal denervation for resistant hypertension. New England Journal of Medicine, 370(15), 1393-1401. (Submitted as Exhibit Q to the DiBona Declaration).
Schaeffer, A. J., Kurtz, M. P., Logvinenko, T., Mccartin, M. T., Prabhu, S. P., Nelson, C. P., & Chow, J. S. (2016). MRI-based reference range for the renal pelvis anterior-posterior diameter in children ages 0-19 years. The British journal of radiology, 89(1067), 20160211. (Submitted as Exhibit R to the DiBona Declaration).

(56) References Cited

OTHER PUBLICATIONS

Weber, M. A., Hering, D., Nikoleishvili, D., Imedadze, A., Dughashvili, G., Klimiashvili, Z., . . . & Provanzano, R. (2023). Durability of the Blood Pressure Effects of Renal Pelvis Denervation in Patients with Hypertension During a 12-Month Observation. American Journal of Nephrology. (Submitted as Exhibit S to the DiBona Declaration).

\* cited by examiner

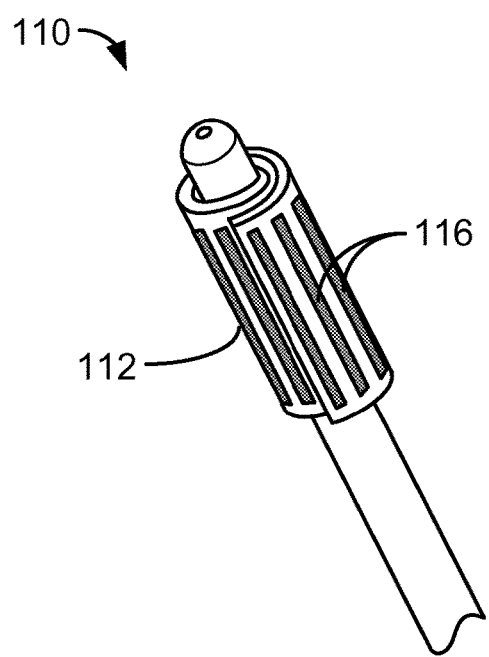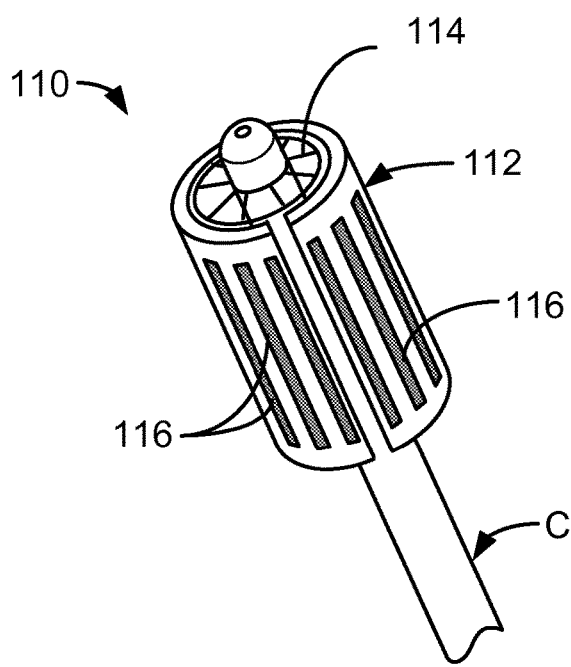
FIG. 9A  FIG. 9B

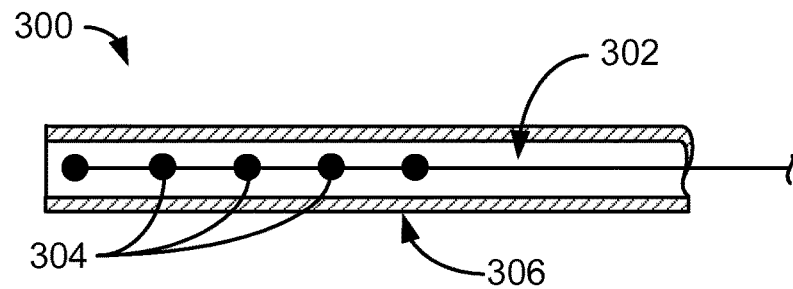
FIG. 27A
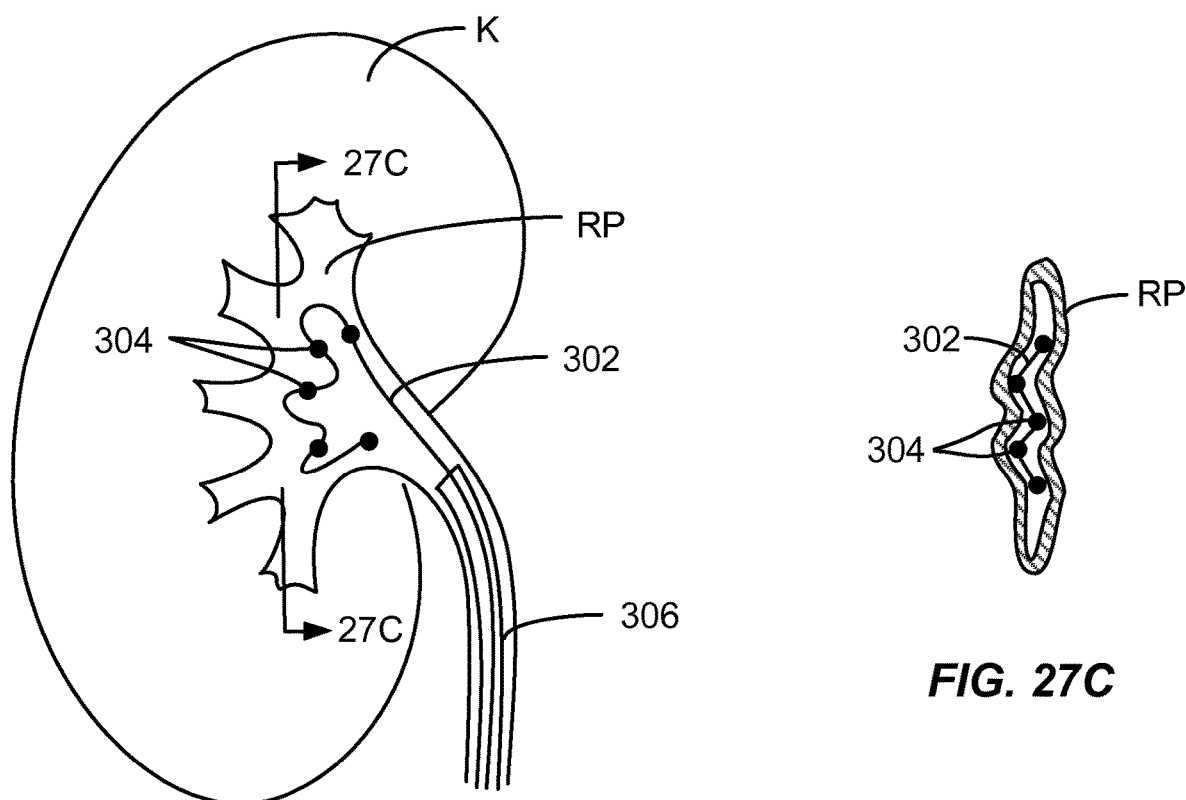
FIG. 27B
FIG. 27C

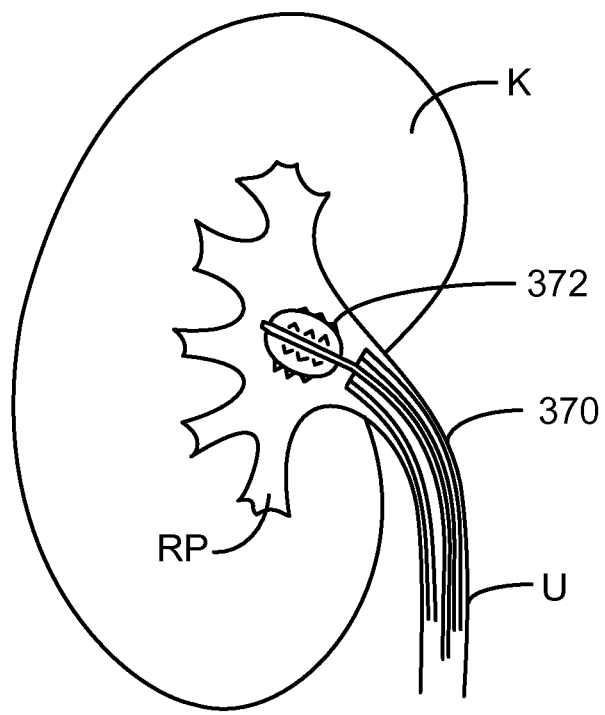
FIG. 34C
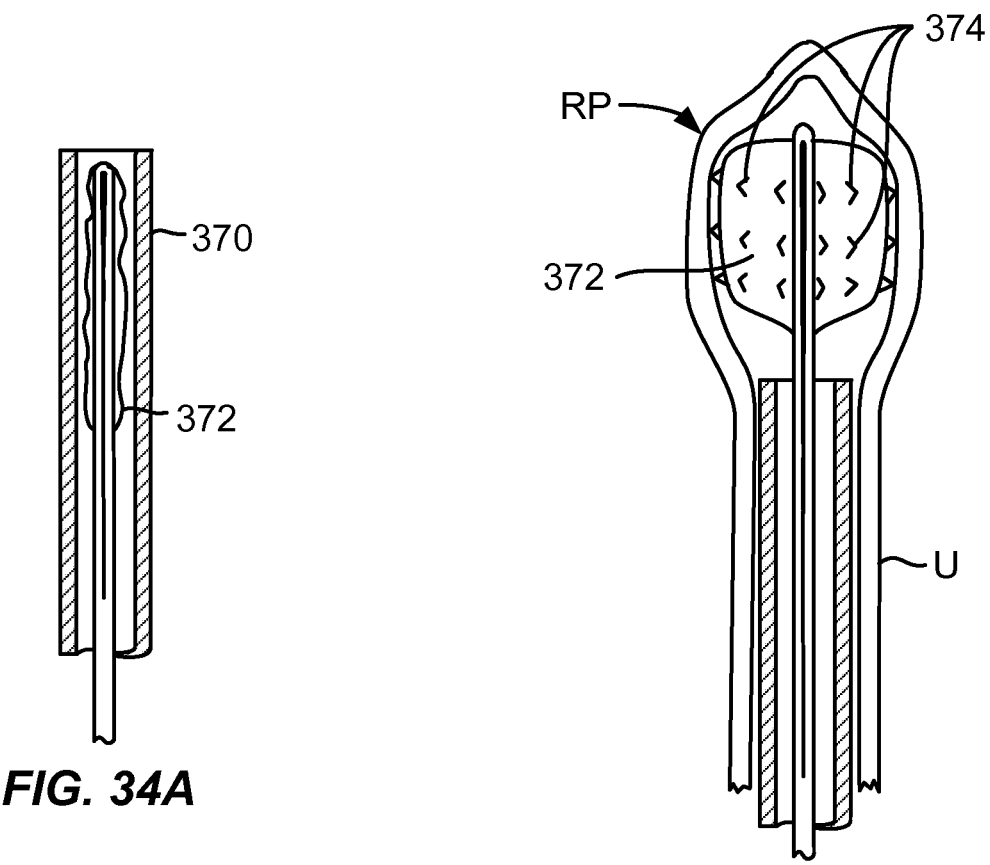
FIG. 34A
FIG. 34B

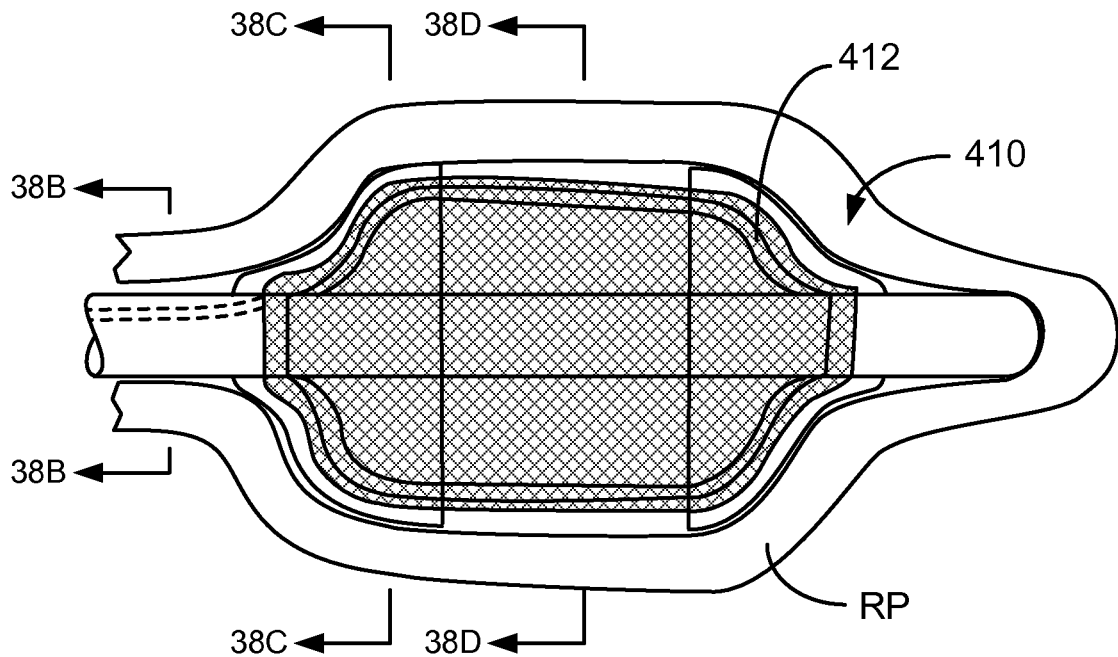
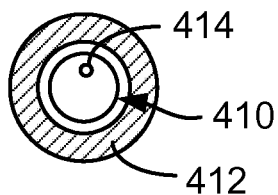
*FIG. 38B*
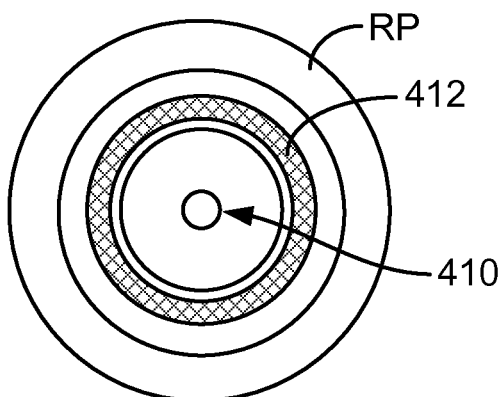
*FIG. 38C*
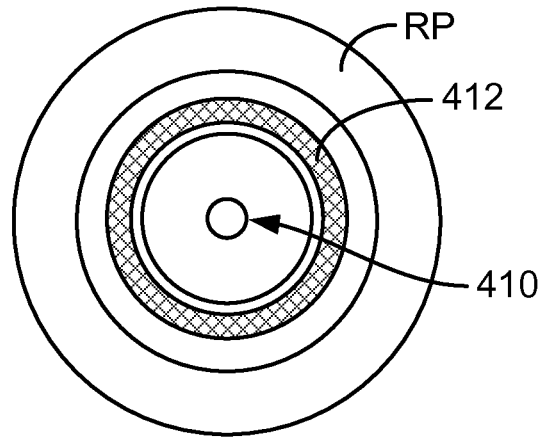
*FIG. 38D*
*FIG. 38A*

METHODS AND SYSTEMS FOR ABLATION OF THE RENAL PELVIS

CROSS-REFERENCE TO RELATED APPLICATIONS

This application is a divisional application of U.S. patent application Ser. No. 14/616,576, filed Feb. 6, 2015, which claims the benefit of the following three provisional patent applications: 61/937,353, filed Feb. 7, 2014; 62/003,918, filed May 28, 2014; and 62/074,894, filed Nov. 4, 2014; the entire contents of each of these applications are incorporated herein by reference.

BACKGROUND OF THE INVENTION

1. Field of the Invention

The present invention relates generally to medical devices, systems, apparatus, and methods for modifying nerve function and treating disease. More particularly, the present invention relates to methods and apparatus for delivering into or through the renal pelvis to modify sympathetic nerve activity in the adventitia of arteries and/or veins that surround the external surface of the renal pelvis in the kidney and in the afferent and efferent nerves within the muscle layers, urothelium and submucosa of the renal pelvis.

Hypertension, or high blood pressure, is a significant and growing health risk throughout the world. Hypertension can be caused by hyperactive renal sympathetic nerves which extend adjacent to the outside of the arteries and veins leading to a patient's kidney as well as within the wall of the renal pelvis. Renal nerve activity can be a significant cause of systemic hypertension, and it has long been known that disrupting renal nerve function can reduce blood pressure. More recently, hypertension therapies based on disrupting the renal nerves surrounding the renal arteries leading to the kidney (renal denervation) have been proposed and are described in the medical and patent literature.

Heretofore, most of the proposed renal denervation therapies have utilized an intravascular approach where a catheter is introduced into the arterial system and advanced to the main renal artery leading to the left or right kidney. Once located at a desired target site within the main renal artery, the catheter is used to deliver radiofrequency energy, heat, drugs, or the like to disrupt the function of the renal nerves which surround the artery. While effective, these techniques present a risk of injury to the renal artery and suffer from all the known disadvantages associated with intravascular access and therapies.

As an alternative to renal denervation through the renal arties, ablation of the renal nerves through the renal pelvis has been proposed. Access to the renal pelvis can be obtained via the ureter, thus avoiding the need to perform intravascular procedures altogether.

For these reasons, it would be desirable to provide alternative protocols and apparatus for performing denervation or other renal nerve function disruptions via the renal pelvis. It would be further desirable if such protocols and apparatus could be performed minimally invasively, would present a reduced risk of injury and trauma to the patient, were economical, and could be performed using simplified and scalable methods. At least some of these objectives will be met by the inventions described herein below.

2. Description of the Background Art

U.S. Patent Publication Nos. 2011/0301662; 2013/0053732; and 2013/0178824 and WO2012/170482 describe apparatus, systems, and methods for ablating or modulating nerves or tissue via the renal pelvis. U.S. Patent Publication No. 2011/0060324 describes apparatus, systems, and methods for performing thermally-induced renal neuromodulation by intravascular access. U.S. Patent Publication No. 2011/0104061 describes apparatus, systems, and methods for active agents to the renal arteries for achieving renal denervation. Published PCT Application WO2010/067360 describes methods and apparatus for modifying blood pressure and kidney function via stimulation of the urinary tract by stimulating the renal nerves. U.S. Pat. No. 8,548,600 describes an intravascular electrode device for delivering energy which may include cylindrical electrodes on a helical deployment wire.

BRIEF SUMMARY OF THE INVENTION

The present invention provides apparatus, systems, and methods for disrupting, inhibiting, denervating and/or modulating the activity of renal nerves present in a patient's kidney by exchanging energy or delivering active agents or substances to the renal wall or the nerves which lie within the wall of the renal pelvis or adjacent to the renal pelvis within the kidney. Most commonly, such renal denervation and/or modulation will be for the purpose of reducing blood pressure in patients suffering from and/or diagnosed with hypertension, but the methods and apparatus of the present invention could be used for treating patients diagnosed with other conditions as described below. The energy exchange is effected through a wall of the renal pelvis using an effector which has been positioned within the interior of the renal pelvis. The renal blood vessels, including the renal arteries and to a lesser extent the renal veins, enter the kidney in a branching network from the main renal artery and main renal vein leading to the kidney. The renal nerves are present in the adventitial tissue surrounding these branching blood vessels as well as in the tissue bed adjacent to the external wall of the renal pelvis. The renal nerves are also in the wall of the renal pelvis in the form of a dense nerve matrix consisting of both afferent and efferent nerves between the muscle layers as well as within the endothelium and submucosa.

The wall of the renal pelvis is a particularly rich source for afferent sensory nerves which are found in the urothelium which lies immediately adjacent to the renal pelvis. They are also found in rich supply in the intermediate submucosal layer which is closest to the urothelium. The renal pelvis wall is also a source for efferent nerves which are found in both the intermediate and outer submucosal layers. Thus, the treatments of the present invention which exchange energy or deliver active agents from the renal pelvis may be particularly effective in treating the afferent sensory nerves which are presently believed to be principally responsible for the reduction of hypertension.

Some embodiments rely on introducing or advancing the effector into the interior of the renal pelvis by a minimally invasive approach or access. Usually the access will be through the urinary tract and thus not require percutaneous penetration (and thus may be performed as a "natural orifice surgery"). Once in the interior of the renal pelvis, the effector will be used to exchange energy and/or deliver active agents or substances to the wall of the renal pelvis and additionally to the tissue bed surrounding the exterior wall of the renal pelvis to effect nerve denervation or modulation. Often, the effector will be an expandable structure, such as an inflatable balloon or mechanically expandable cage, which can be deployed within the renal pelvis to engage at least a portion of interior wall of the renal pelvis, often engaging the entire interior wall of the renal pelvis. Elements for exchanging energy and/or delivering active substances can be present on the outer wall of such expandable structures or may be present within the interior of such expandable structures in order to generate, exchange, and deliver energy and substances as described in more detail below.

The effector may be advanced to the interior of the renal pelvis of the kidney in a variety of ways. Usually, the effector will be advanced through the urinary tract to reach the renal pelvis without the need to penetrate tissue. In such cases, the effector will be disposed on a urinary catheter, typically near a distal end of the catheter, and the urinary catheter will be advanced through the urethra, the bladder, and the ureter to reach the renal pelvis. Techniques for advancing catheters into the renal pelvis are known in the art, for example in connection with delivery of urinary stents to create drainage paths past urinary stones. Usually, an access or guide catheter and/or a guidewire will be placed through the urethra into the bladder to provide an access path through the os of the ureter at a proximal end of the bladder. A second catheter carrying the effector will then be advanced through the access or guide catheter and/or over the guidewire and then through the length of the ureter so that the effector is position within the interior of the renal pelvis. The effector will usually be expanded and then be used to exchange energy and/or deliver active substances, as described in greater detail below.

A number of specific devices and methods may be employed using the effector in order to denervate, modulate, or inhibit the renal nerves within the wall of the pelvis or surrounding the renal pelvis. For example, the effector may comprise electrodes, typically on an inflatable or expandable structure, and the electrodes may be used to deliver radiofrequency energy across the wall of the renal pelvis to treat the nerves within the wall of the renal pelvis and/or further into the nerves surrounding the renal pelvis to heat the tissue bed surrounding the pelvis to treat the renal nerves. The electrodes may be monopolar, in which case the "active" electrodes on the effector will be connected to one pole of a radiofrequency generator while the other pole will be connected to a dispersive electrode placed on the patient's skin, typically on the small of the back. Alternatively, the radiofrequency electrodes could be bipolar, where one or more electrode pairs (nominally positive and negative) are disposed on the surface of the effector in order to deliver a more localized and higher current density to the tissue surrounding the renal pelvis to treat the nerves within the wall of the renal pelvis and/or further into the nerves surrounding the renal pelvis.

In a second aspect, some embodiments provide apparatus and systems for inhibiting, modulating, or destroying function of renal nerves in a patient's kidney. Apparatus comprise a catheter adapted to be introduced into an interior of the kidney, typically the renal pelvis, and an effector on the catheter to exchange energy and/or deliver an active substance from the interior of the kidney through a wall of the renal pelvis into the nerves within the wall of the renal pelvis surrounding the renal blood vessels in the kidney. The effector will typically comprise an expandable member which can be expanded within the renal pelvis to engage an interior wall of the renal pelvis, for example, comprising a compliant balloon or mechanically expandable cage adapted to inflate/expand to occupy all or a substantial portion of the interior volume of the renal pelvis. The compliant balloon or other expandable structure can thus serve to position elements of the effector against the interior wall of the renal pelvis and/or to locate an internal mechanism within the effector in a predetermined position/geometry relative to the wall and nerves of the renal pelvis. Usually, the effector will be adapted to limit the exchange of energy and/or the delivery of active substances into regions of the kidney beyond the renal pelvis, such as the papillae, the pyramids, the parenchyma, and other sensitive structures of the kidney which could be damaged by the protocols herein and adversely impact kidney function. While the inflatable body or other portions of the effector could engage such sensitive structures, the effector will be designed so that energy exchange and/or active substance delivery avoid such sensitive structures, for example by placing external elements on the effector away from such sensitive structures.

In one specific aspect of the present invention, a method for inhibiting or modulating the function of renal nerves in a patient's kidney comprises introducing an effector into an interior of the kidney or an upper region of an adjacent ureter. Energy is exchanged and/or active substances are delivered from the interior of the kidney to ablate a layer of tissue lining at least a portion of the renal pelvis to disrupt renal nerves within the tissue lining of the renal pelvis. The tissue lining comprises a urothelium, a lamina propria, and two muscle layers, and ablation occurs primarily within the urothelium and the lamina propria. In some instances, the ablation may extend into a connective tissue and vascular layer that surrounds the lamina propria. Typically, the ablation extends to a depth in the range from 0.1 mm to 2 mm, preferably from 0.2 mm to 1.5 mm, and more preferably from 0.5 mm to 1.2 mm. In specific embodiments, electrical energy is delivered uniformly over a continuous region of the renal pelvis at a power in the range from 50 W to 200 W.

In another specific aspect of the present invention, apparatus, systems, and methods for disrupting, inhibiting, denervating and/or modulating the activity of renal nerves present in a patient's kidney deliver specific patterns of energy through the renal pelvis wall and to the renal nerves which lie within the wall of the renal pelvis or adjacent to the renal pelvis within the kidney. In particular, the present invention comprises an insulated electrode structure comprising a helical, preferably spiral, electrode deployment structure, typically a pre-shaped wire, which carries rounded, ovoid, or spherical electrodes for engaging and delivering electrical energy to tissue of or near the renal pelvis or other luminal and cavity-like body structures.

Such devices are particularly advantageous as they may be easily positioned by a steerable or other sheath to position the balls or other point electrodes in the center of the renal pelvis, or any other desired location. Since the sheath and the device are not locked together, the device can be rotated relative to the sheath. This allows the sheath to maintain its curve while the helix is rotated for better positioning.

The diameter of the balls is significantly larger than an outside diameter (OD) of the insulation on the supporting wire. An exemplary design has a ratio of 3.4:1 (0.078 in to 0.023 in) which allows the tissue to conform around the electrodes, ensuring that the electrodes will have a large contact surface area and excellent tissue contact. The geometry also helps guarantee a larger electrode-to tissue contact force. The larger contact surface area, improved electrode/tissue contact, and larger electrode/tissue contact force are all desirable for safe, proper, and efficient energy delivery and lesion geometry. The helical/spiral shape of the device will cause the balls to press against the walls of the renal pelvis. The spacing of the balls and the helical shape creates discrete lesions in the renal pelvis on different tissue planes.

This ensures that there is enough healthy tissue left intact so that the pelvis and ureter do not stricture significantly.

In a first aspect of the present invention, a method for inhibiting or modulating the function of renal nerves in a patient's kidney comprises introducing an effector into an interior of the kidney or an upper region of an adjacent ureter. Energy is exchanged or active substances delivered from effector in the interior of the kidney to ablate a layer of tissue lining at least a portion of the renal pelvis to disrupt renal nerves within the tissue lining and optionally muscle layers of the renal pelvis. The layer typically includes the urothelium and the lamina propria. While the ablation occurs primarily within the urothelium and the lamina propria, in some instances ablation can extends into connective tissue and a vascular layer that surrounds the lamina propria and muscle layers.

The depth of ablation is controlled to achieve a desired ablation with minimal damage to the kidney and kidney function. Typically, the ablation extends to a depth in the range from 0.1 mm to 2 mm, usually from 0.2 mm to 1.5 mm, and often from 0.5 mm to 1.2 mm. Such ablation depth can be achieved by delivering electrical energy, typically radiofrequency current, over a continuous region of the renal pelvis at a power in the range from 1 W to 200 W.

Introducing the effector may comprise advancing the effector through the urinary tract to the renal pelvis. For example, the effector may be disposed on a urinary catheter, and the urinary catheter may be advanced through the urethra, bladder, and ureter to reach the renal pelvis. Alternatively, introducing the effector may comprise advancing the effector percutaneously to the renal pelvis.

Energy may be delivered in a variety of ways. For example, the effector may comprise electrodes and the energy may comprise radiofrequency energy which is delivered to heat the wall of the renal pelvis and renal nerves embedded in the tissue bed surrounding the renal blood vessels. Alternatively, the effector may comprise an antenna and the energy may comprise microwave energy which is delivered to heat the wall of the renal pelvis and renal nerves embedded in the tissue bed surrounding the renal blood vessels. Further alternatively, the effector may comprise an ultrasound transducer and the energy may comprise ultrasound energy which is delivered to heat the wall of the renal pelvis and renal nerves embedded in the tissue bed surrounding the renal blood vessels. As a specific example of ultrasound energy, the ultrasound transducer may comprise a high intensity focused ultrasound transducer array. Other energy effectors may comprise a convective heat source which delivers heat through the renal pelvis to heat the wall of the renal pelvis and renal nerves embedded in the tissue bed surrounding the renal blood vessels. A specific example of a convective heat source would deliver a heated fluid within an inflated chamber deployed within the renal pelvis. Conversely, the effector may comprises a convective cooling source where heat is extracted through the renal pelvis to cool the wall of the renal pelvis and renal nerves embedded in the tissue bed surrounding the renal blood vessels. An exemplary convective cooling source comprises a cooled fluid deployed within an inflated chamber within the renal pelvis. Still other effectors may comprise a radiation-emitting source, either a radioisotope or an X-ray or other electronic radiation. Other examples include effectors having tissue-penetrating electrodes which are penetrated into a wall of the renal pelvis while energy is delivered to the wall through the electrodes. In yet other examples, the energy exchanged is mechanical energy such as abrasion or cutting.

In a second aspect of the present invention, an electrode structure comprises a self-expanding deployment wire having a distal region configured to expand into and engage a wall of a renal pelvis. A plurality of rounded electrode members is distributed over said distal region where each rounded electrode member has a surface which extends radially outwardly beyond the surface of the adjacent wire.

The distal region of the deployment wire typically has a three-dimensional expanded geometry, such as a helical or spiral distal geometry or may have a two-dimensional geometry, such as a looped distal end. Even lop structures, hover, may have secondary structures, such a bending or local coiling, to impart a third dimension to a planar geometry. Typically, at least the distal region of the deployment wire is electrically insulated over its surface between the rounded electrodes. The diameter of the rounded electrode structure may be from two-fold to six-fold greater than that of the deployment wire, and exemplary electrode will have a deployment wire diameter in the range from 0.1 mm to 7 mm and a rounded electrode member diameter in the range from 0.25 mm to 2.5 mm. In specific embodiments, the rounded electrodes are ball electrodes.

The electrode structures are frequently incorporated in an electrode deployment assembly which comprises the electrode structure as above with a delivery tube having a central, passage. The electrode structure is reciprocatably received the central passage of the delivery, wherein the distal region of the deployment wire is radially constrained when present in the passage and radially expanded when advanced distally out of the passage. The electrode structure is usually free to rotate in the passage of the delivery tube.

In a third aspect of the present invention, a method for delivering energy to a renal pelvis comprises introducing a wire into the ureter adjacent to or within the renal pelvis. The wire has a pre-shaped distal region configured to conform to the renal pelvis. The distal portion of the wire is advanced into the renal pelvis, wherein the distal portion is radially constrained while being advanced, and the distal region of the wire is released from constraint within the renal pelvis to engage tissue over a wall of the renal pelvis. Energy is applied to the wall of the renal pelvis through a plurality of electrodes on the wire, wherein the electrodes have rounded surfaces (typically being ball electrodes) which extend beyond the surface of the adjacent wire and which embed into the renal pelvis wall.

In exemplary embodiments, a vacuum may be applied within the renal pelvis while applying energy to draw the walls of the renal pelvis against the rounded electrodes. The pre-shaped distal region of the wire may have a helical, spiral, looped or other two-dimensional or three-dimensional distal geometry. At least the pre-shaped distal region of the wire will usually be electrically insulated over its surface between the electrodes, and the diameter of the electrodes will usually be from two-fold to six-fold greater than that of the wire. In specific embodiments, the wire has a diameter in the range set forth above and the electrodes have a diameter in the range set forth above. In an exemplary protocol, the distal portion of the wire is advanced into the renal pelvis from a central passage of a delivery tube which had been positioned in the renal pelvis, wherein the distal region is radially constrained when present in the passage and radially expanded when advanced distally out of the passage.

BRIEF DESCRIPTION OF THE DRAWINGS

The novel features of the invention are set forth with particularity in the appended claims. A better understanding of the features and advantages of the present invention will be obtained by reference to the following drawings and detailed written description that set forth illustrative embodiments in which the principles of the invention are utilized.

FIGS. 9A and 9B illustrate an alternative device configured to ablate one or more tissue layers of the renal pelvic wall.

FIGS. 27A-27C show ball electrodes attached to superelastic alloy wire inside a catheter tube and subsequently deployed in a renal pelvis.

FIGS. 34A-34C show a drug delivery balloon with microspikes both inside a sheath and deployed in the renal pelvis.

FIGS. 38A-38D show a drug delivery catheter with mesh, silicone, and balloon components.

DETAILED DESCRIPTION OF THE INVENTION

Figure 1:
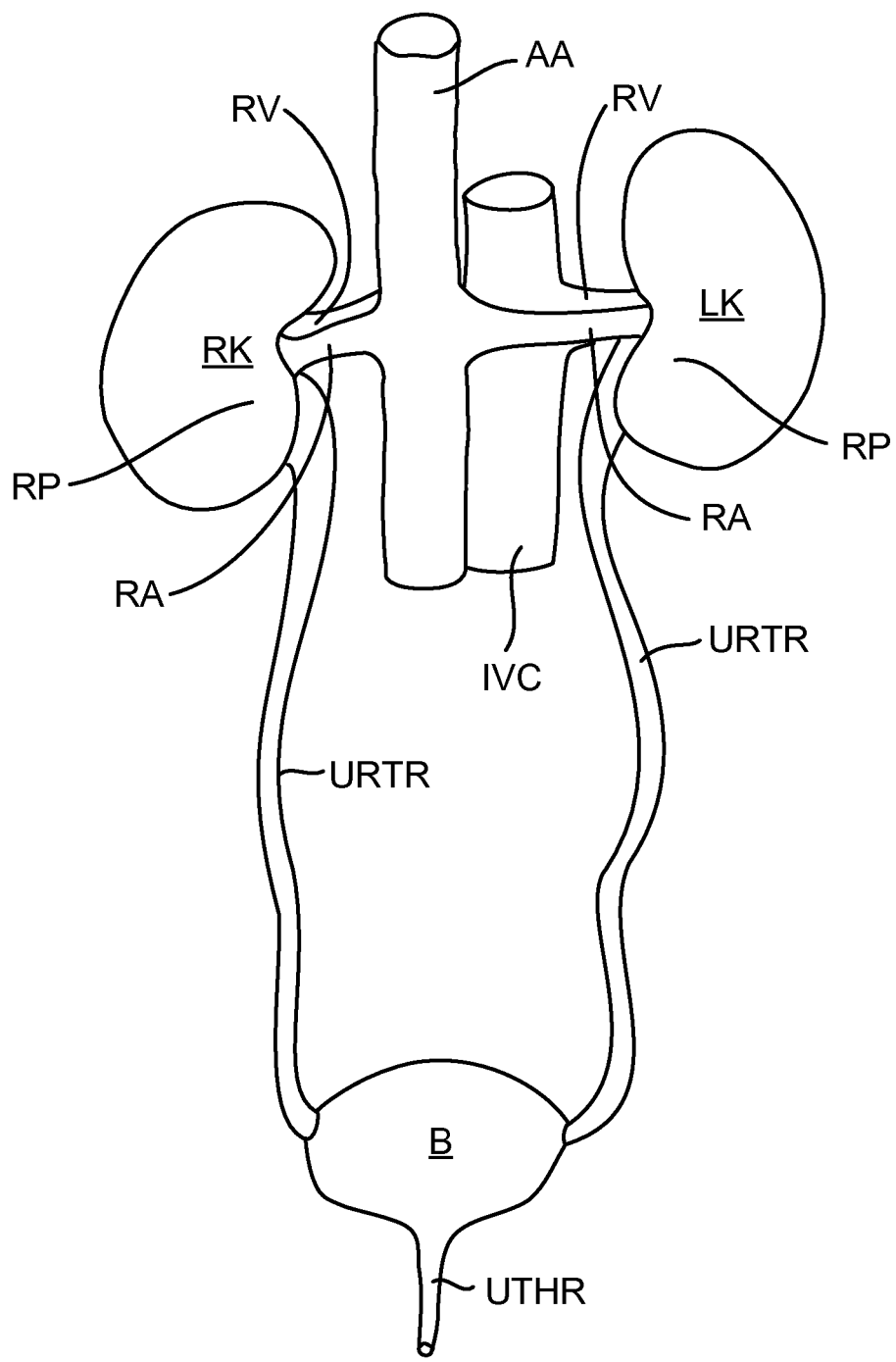
FIG. 1 is a diagrammatic illustration of a patient's urinary system.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

A patient's urinary tract is diagrammatically illustrated in FIG. 1. The urinary tract includes the bladder B, which receives urine from the right and left kidneys RK and LK and drains the urine through the urethra UTHR. The kidneys each receive oxygenated blood through the renal artery RA from the abdominal aorta AA and blood from the kidneys is returned through the renal vein RV to the inferior vena cava IVC. Of particular interest to the present invention, the urine which is processed in the kidney is received in an interior cavity of each kidney referred to as the renal pelvis RP which acts as a funnel and delivers the urine into the top of the ureter URTR. The methods and protocols of the present invention will be performed within the interior of the renal pelvis RP in order to treat the renal nerves within the walls of the renal pelvis as well as the nerves surrounding the renal arteries within the adventitia and adipose tissue and to a lesser extent surrounding the renal veins which branch from the main renal artery and renal vein within the tissue of the kidney.

Figure 2A:
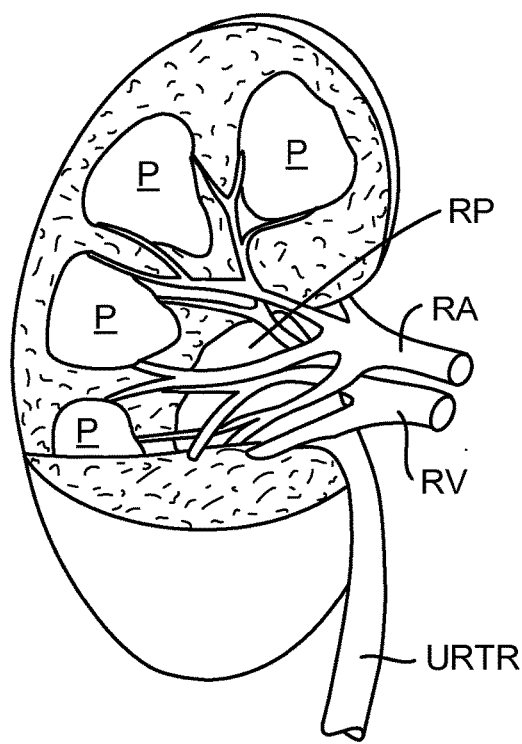
FIGS. 2A and 2B are partially broken-away illustrations of a patient's kidney showing the renal pelvis and other structures.
Figure 2B:
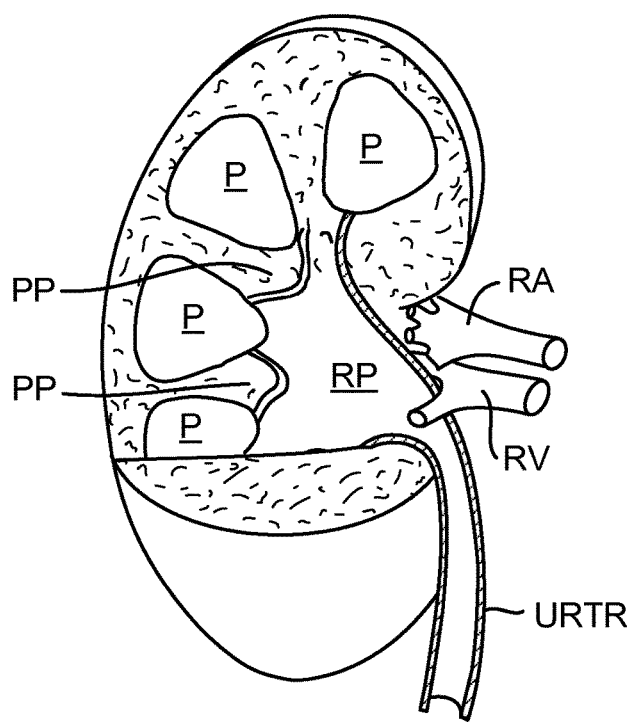
Figure 3:
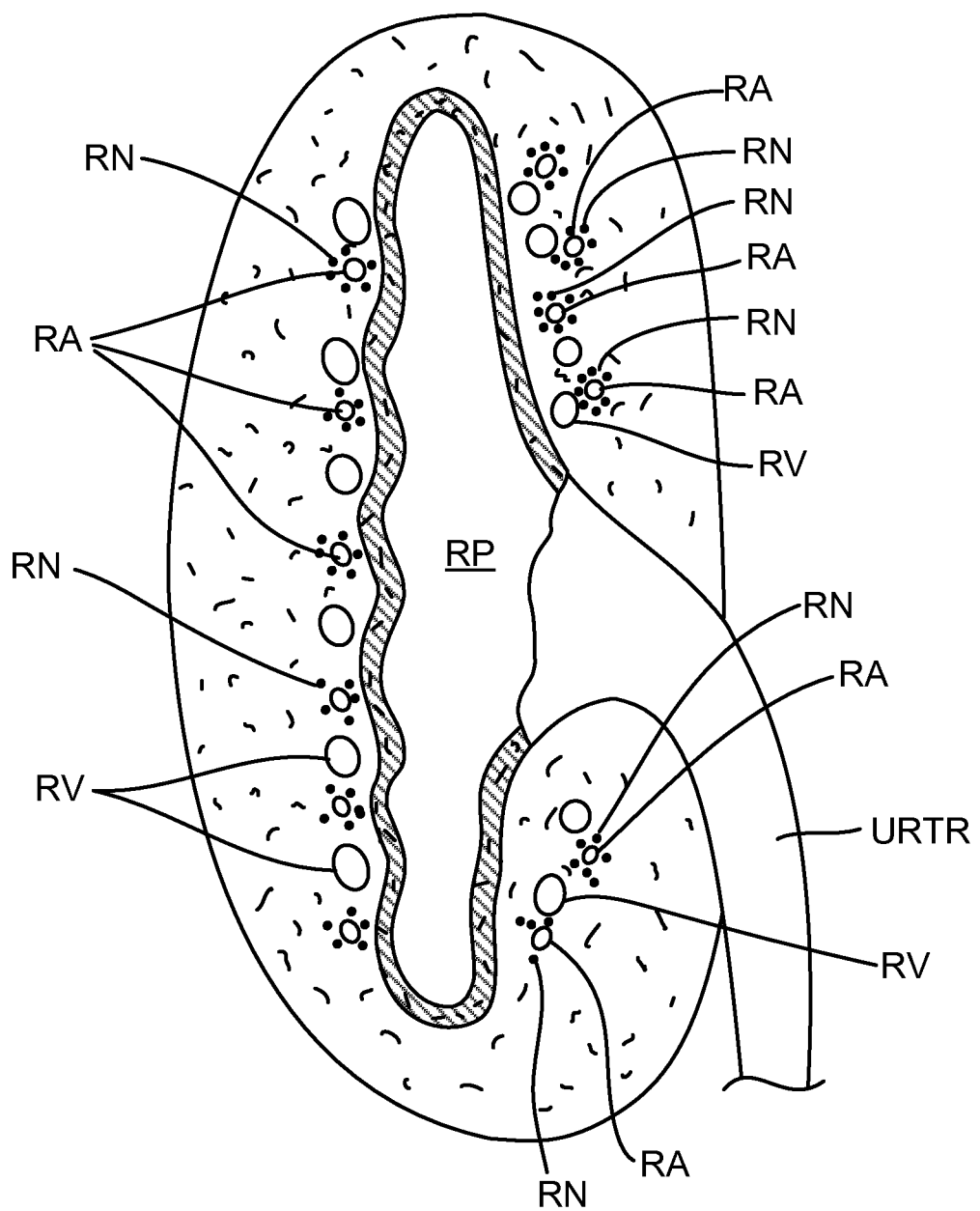
FIG. 3 is a cross-sectional view of the patient's kidney taken along line 3-3 of FIG. 2A.
Figure 3A:
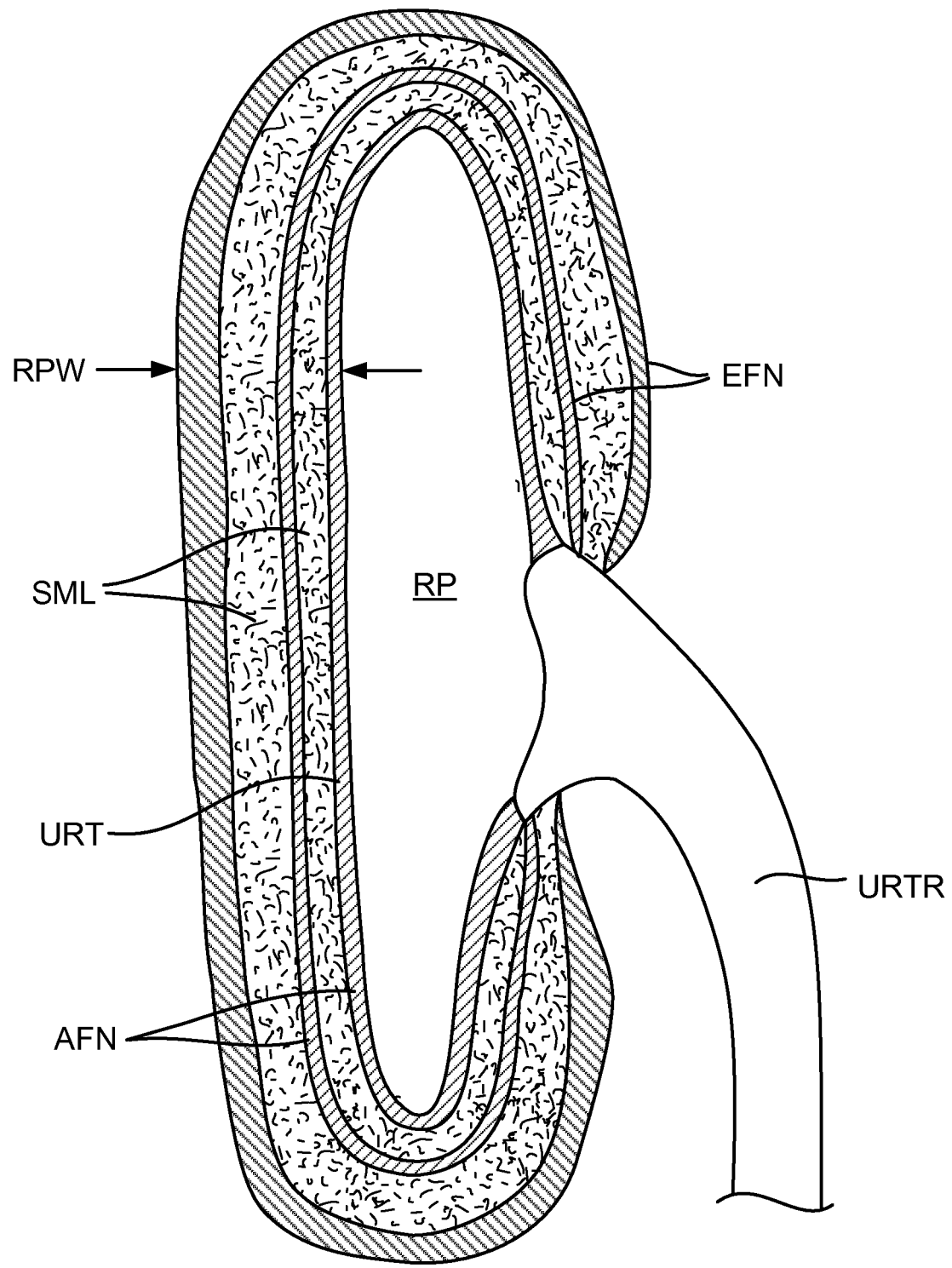
FIG. 3A shows the structure and location of renal nerves within the muscle layers, endothelium and submucosa of the renal pelvis. The afferent nerves originate and are mostly contained within the wall of the renal pelvis. They have a direct effect on the efferent sympathetic nerves and are responsible for sympathetic muscle tone and vasoconstriction.

Referring now to FIGS. 2A and 2B, the right kidney RK is shown in section to expose the renal pelvis RP and other internal structures of the kidney. As shown in FIG. 2A, the renal pelvis is a funnel-shaped extension of the upper and of the ureter URTR and is surrounded by the branching portions of the renal artery RA and the renal vein RV, both of which branching structures extend into the body of the kidney and surround the pyramids P and other structures, including the papillae PP. The branching structures of the renal artery RA and renal vein RV as well as the anterior wall of the renal pelvis are removed in FIG. 2B to show the interior of the renal pelvis which is the target location for the therapies of the present invention As further shown in FIG. 3 which is a cross-sectional view taken along line 3-3 of FIG. 2A, the renal nerves RN surround the renal blood vessels, particularly the renal arteries RA, extending adjacent to and surrounding the outer wall of the renal pelvis RP in a tissue bed surrounding the renal pelvis. As shown in FIG. 3A, the renal nerves follow the arteries and then divide. A portion of the divided nerves enter the renal pelvic wall RPW where they intertwine with the afferent nerves AFN that are located within the smooth muscle layers, endothelium and submucosa SML of the renal pelvis. The afferent nerves AFN originate and are mostly contained within an interior wall of the renal pelvis adjacent to the urothelium URT. The afferent nerves have a direct effect on the efferent sympathetic nerves EFN (which are generally located nearer the exterior surface of the renal pelvis wall RPW than are the afferent sensory nerves AFN) and are responsible for sympathetic muscle tone and vasoconstriction. It is the renal nerves shown in FIGS. 3 and 3A, and in particular the sensory afferent nerves AFN, which are typically but not exclusively the target structures to be treated by the methods and apparatus of the present invention.

Figure 4A:
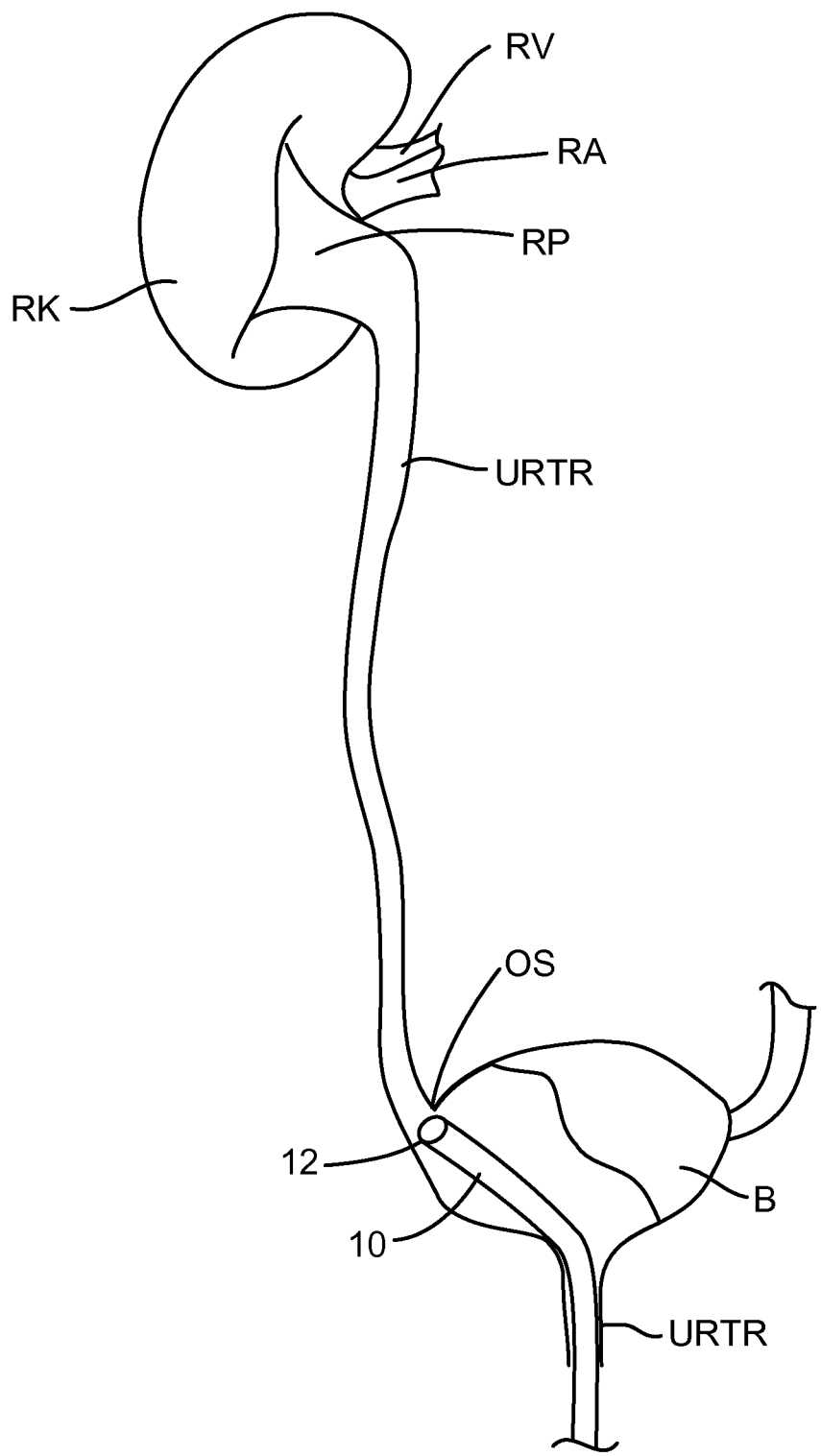
FIGS. 4A through 4C illustrate access and treatment of a patient's renal pelvis according to the principles of the present invention.
Figure 4B:
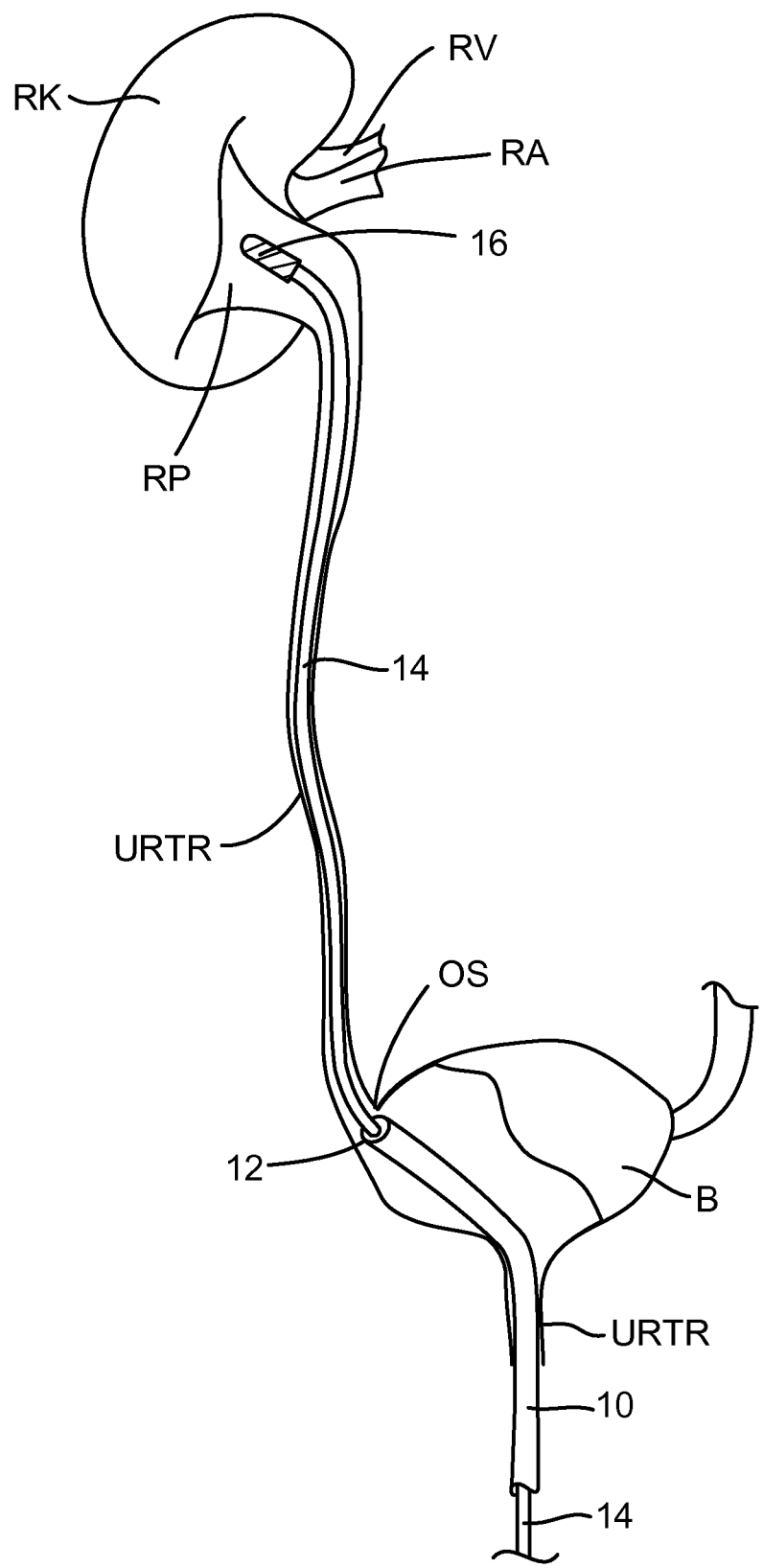
Figure 4C:
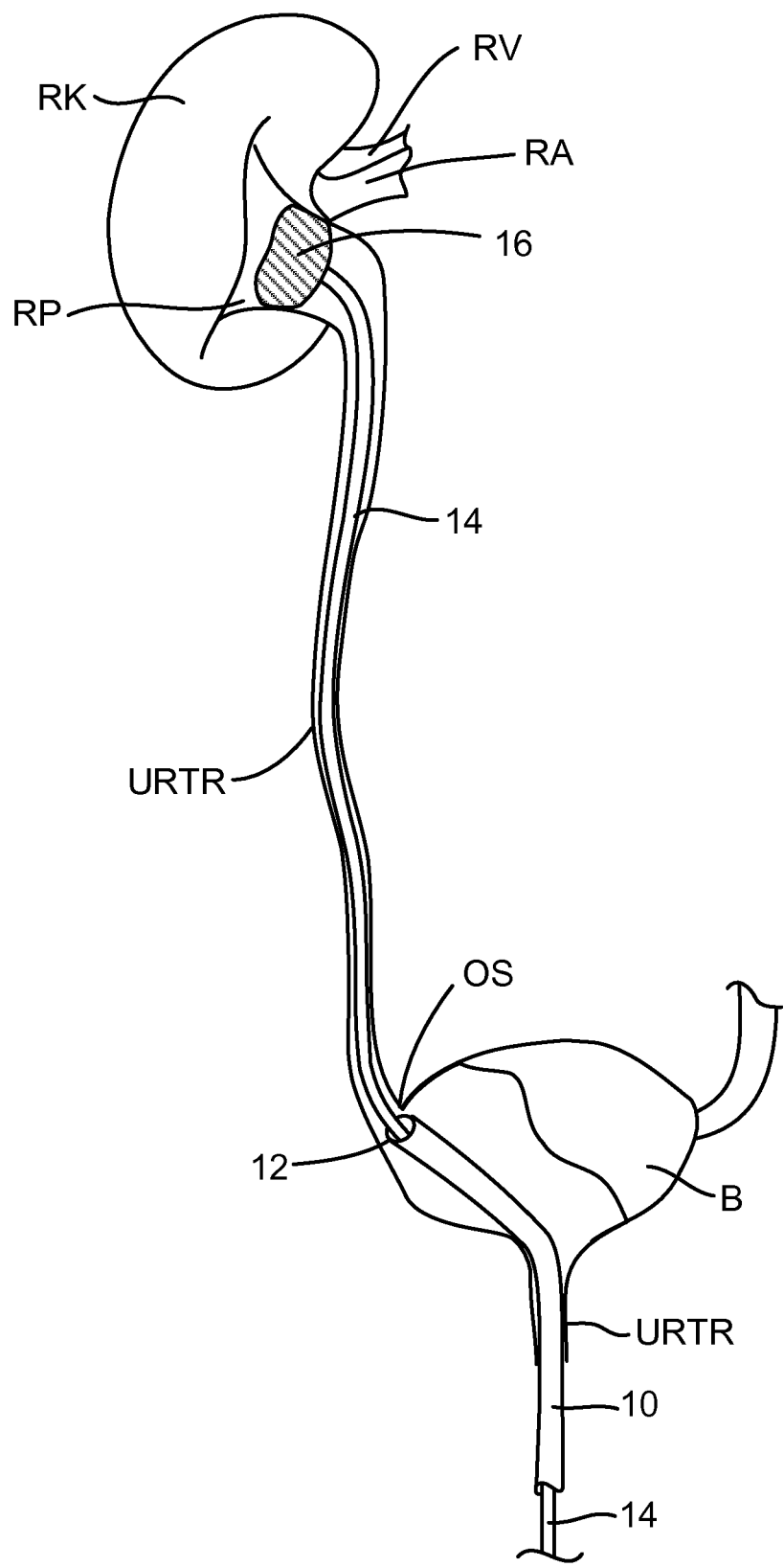

Referring now to FIGS. 4A through 4C, a first exemplary protocol for accessing and treating the renal nerves in the kidney will be described. Initially, a guide or other tubular catheter 10 is advanced through the urethra UTHR to position a distal port 12 adjacent the os OS at the lower end of the ureter URTR.

As shown in FIG. 4B, a treatment catheter 14 is then advanced through the guide catheter 1 (optionally over a guidewire), out of port 12, and into a lumen of the ureter URTR. An effector 16 at the distal end of the treatment catheter 14 is advanced into the renal pelvis RP, optionally under fluoroscopic and/or ultrasound guidance in a conventional manner.

Once in the renal pelvis RP, the effector 16 will be deployed in order to treat the renal nerves in accordance with the principles of the present invention. For example, the effector may comprise an expandable structure which is mechanically expanded or inflated within the renal pelvis to engage the interior walls of the pelvis as shown FIG. 4C. Any one of a variety of energy exchange devices or substance delivery devices may then be employed to exchange energy or deliver the substances through the wall of the renal pelvis to treat the nerves embedded within the walls.

Figure 5:
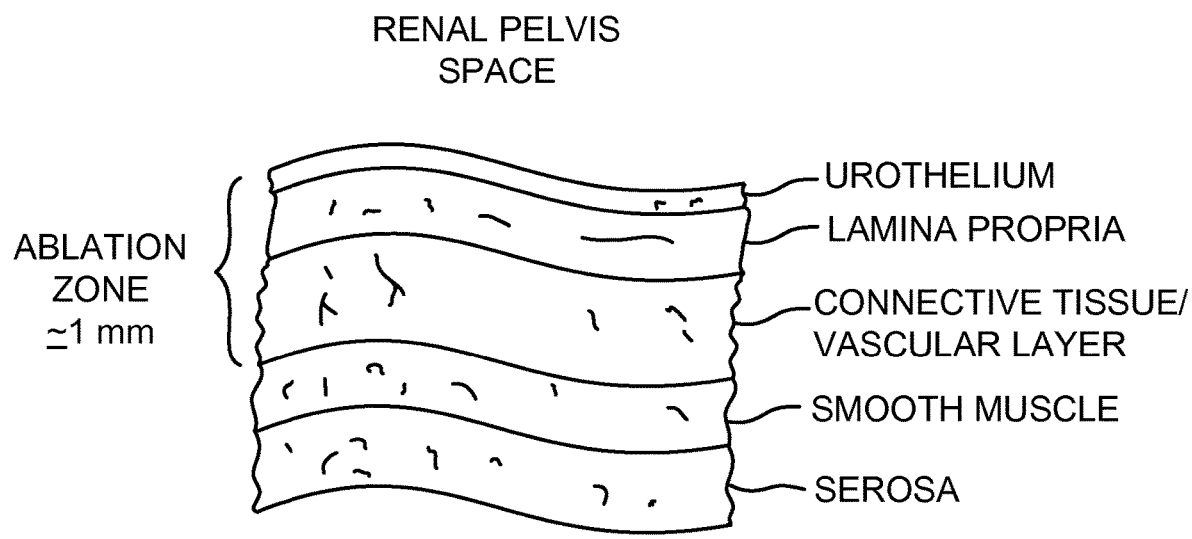
FIG. 5 illustrates the tissue layers of the renal pelvic wall.

In some instances, devices and methods will be configured to ablate a thin layer of tissue which lines the renal pelvis. The renal pelvic wall consists of multiple tissue layers as shown in FIG. 5. Afferent and efferent nerves exist through the layers, and there is a high concentration of afferent nerves close to the surface (e.g., within the urothelium, lamina propria, and extending into a first muscle layer). Together, the urothelium and lamina propria layers will be referred to as the "tissue lining the renal pelvis." The inventors herein have determined that moderate to extensive damage to the muscle layers may cause stenosis of the renal pelvis, which is of course undesirable. The inventors herein have further determined that the creation of very shallow lesions on the interior wall of the renal pelvis will target the surface afferent nerves (thus achieving renal denervation), while leaving the surrounding tissue (muscle, blood vessels, etc.) intact.

This result can be achieved with any number of devices, including those described in commonly owned U.S. Patent Publication 2013/0178824, the full disclosure of which is incorporated herein by reference, as well as a number of other devices described below. Energy or substance delivery through the devices must be carefully controlled to achieve the desired effect. Exemplary protocols will apply RF energy at high power (e.g., 50-200 Watts) and short application times (e.g., 0.1-15 seconds). In other instances, however, it may be possible to achieve similar ablation using low power (e.g., 1-50 Watts) and longer times (e.g., 60-300 seconds). Lesion depth should be between 0.1 mm and 2 mm, usually between 0.2 mm and 1.5 mm, and often between 0.5 mm and 1.2 mm. FIG. 5 shows the ablation zone depth.

Surface lesions having the desired depths can be created by regulating temperature, time, power, and/or impedance. More specifically, the lesion depth can be controlled by applying a specified power until a specified impedance is reached. Alternatively, the lesion depth can be controlled by maintaining a specified temperature for a specified length of time. Under any control algorithm, time, power, temperature, and impedance can be monitored for safety limits.

Figure 6:
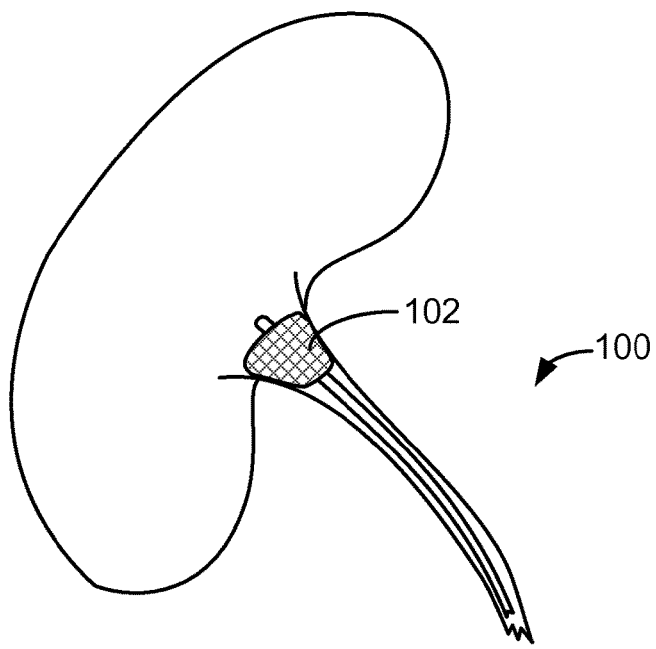
FIG. 6 illustrates a device configured to ablate one or more tissue layers of the renal pelvic wall.
Figure 7:
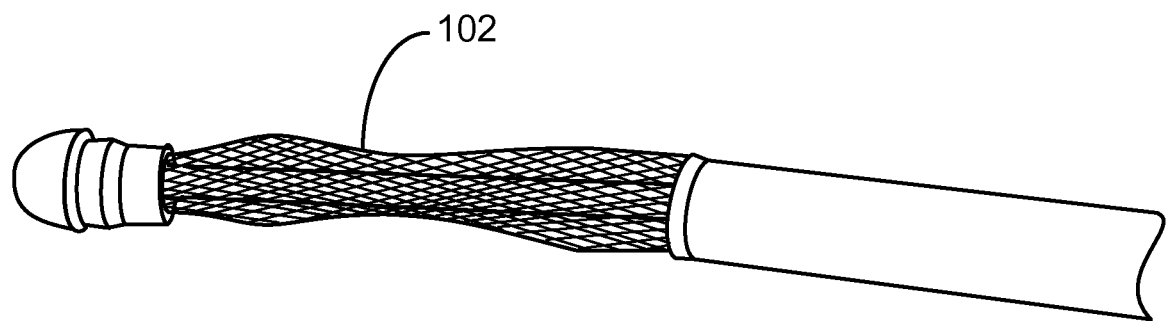
FIGS. 7 and 8 show a mesh electrode of the device of FIG. 6 on its collapsed and expanded configurations, respectively.
Figure 8:
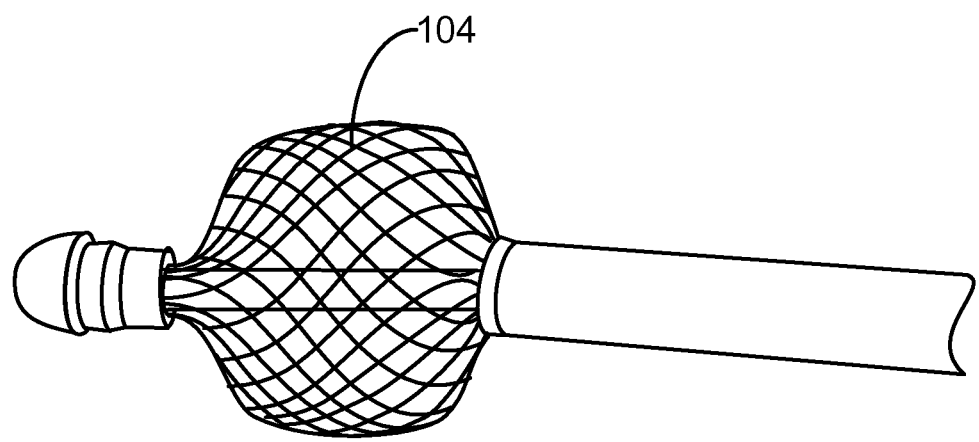

An exemplary device 100 for delivering RF power to the renal pelvis is shown in FIGS. 6-8. The device includes tubular Nitinol® mesh electrode 102 that is expanded at the target site in the renal pelvis, as shown in FIG. 6. Monopolar energy is delivered through all wires of the expanded mesh to create the desired lesion. The diameter of the device is typically 7 Fr-11 Fr in the collapsed state (FIG. 7). The diameter of the mesh is typically 8 mm-20 mm in the expanded state (FIG. 8). The length of the mesh electrode is usually 8-20 mm in the expanded state. Use of a mesh electrode is desirable as it readily conforms to the shape of the renal pelvis.

In other embodiments, the electrodes on the delivery catheter may comprise balloons with conductors formed over their external surfaces, e.g., by conductive inks or conductive wire.

In a further exemplary device 110, an expandable flex circuit 112 can be located over a balloon 114 or other inflatable/radially expandable structure, as shown in FIGS. 9A and 9B. In this design, the flex circuit is initially rolled over the balloon (FIG. 9A), and balloon is inflated to expand and unroll the flex circuit (FIG. 9B) so that electrode(s) 116 and optionally thermocouple(s) (not shown) formed on the exterior surface of the flex circuit contact the renal pelvic wall tissue when the flex circuit is expanded. As an alternative to a rolled-up flex circuit, the flex circuit could have other expandable geometries, such as pleated, patterned (similar to an arterial stent), or the like, so that it is able to expand from a low diameter delivery configuration to a larger diameter deployed configuration. Flex circuit dimensions are typically 7 Fr-11 Fr in the collapsed state (FIG. 9A) and 8-20 mm diameter and 8-20 mm length in the expanded state (FIG. 9B). These designs can be monopolar or bipolar, the latter being useful in limiting surface lesion depth.

Another approach to creating effective renal denervation lesions without damaging renal pelvic function is to create deeper lesions only in specific areas. This will leave healthy tissue intact, avoiding strictures in the renal pelvis. Multiple devices are disclosed below to achieve this effect.

Figure 10A:
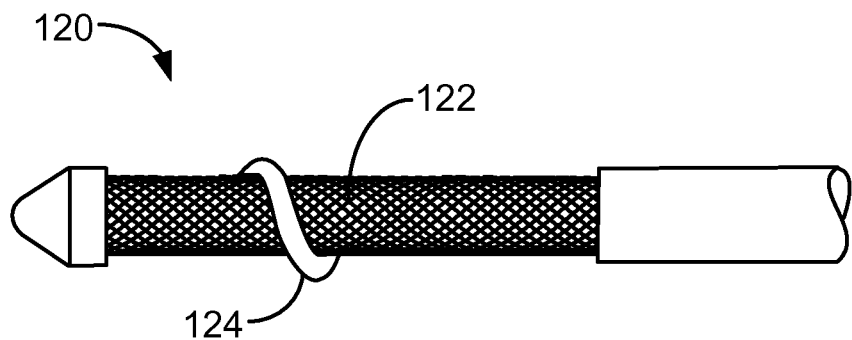
FIGS. 10A-10C illustrate devices configured to create deeper lesions in the renal pelvic wall.
Figure 10B:
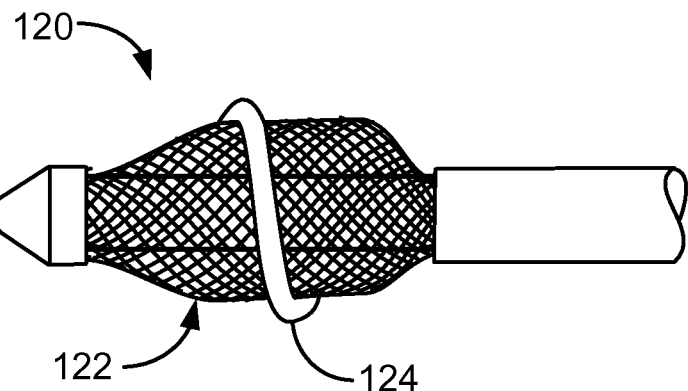
Figure 10C:
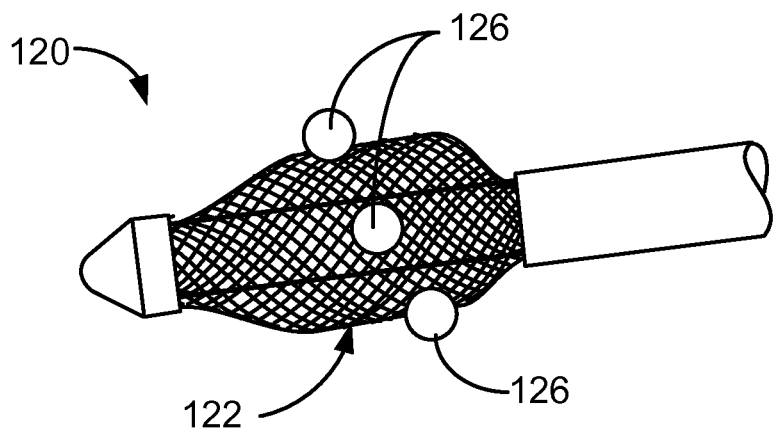

As shown in FIGS. 10A-10C, a device 120 carries a non-conductive, tubular mesh 122 is configured to be expanded and contracted. A helical conductive wire 124 or other conductor is carried over or woven into the non-conductive mesh. For example, the conductive wire may be a stainless steel braid, but in other instances, the conductive wire can be mono- or multi-filament. Delivery of RF or other electrical energy through the helical conductor 124 will create a helical lesion on the renal pelvis. A helical lesion helps ensure that cross-sectional areas will contain only one unique area of tissue damage around the radius. The diameter of the mesh is 7 Fr-11 Fr in the collapsed state (FIG. 10A) and is 8 mm-20 mm in the expanded state (FIG. 10B). The length of the mesh is 8 mm-20 mm in the expanded state. If the conductive wire is a monofilament, the diameter can be from 0.1 mm to 0.5 mm. If the conductive wire is a braided cable or a braided tube, the diameter can be from 0.1 mm to 0.25 mm. A thermocouple may be secured to the conductive wire or to the non-conductive mesh in proximity to the conductive wire for temperature control. Alternatively, lesions can be created with impedance control only.

In a similar embodiment shown in FIG. 10C, conductive contact pads 126 (e.g., metallic balls) are applied to the conductive wire at specific intervals to enhance tissue contact and create non-continuous lesion patterns. The conductive wire is insulated between the contact pads so that only the contact pads conduct energy to the tissue.

Figure 11A:
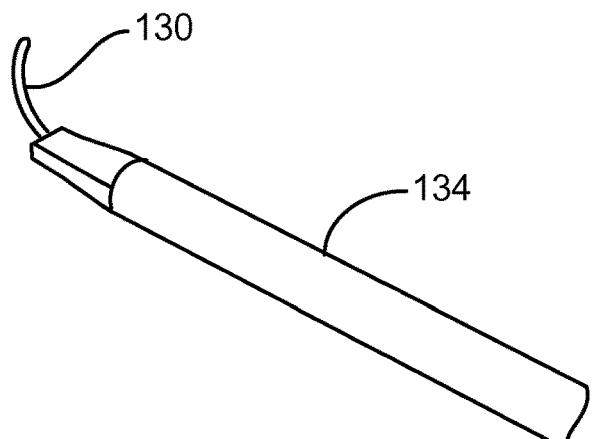
FIGS. 11A-11C illustrate an alternative device configured to create deeper lesions in the renal pelvic wall.
Figure 11B:
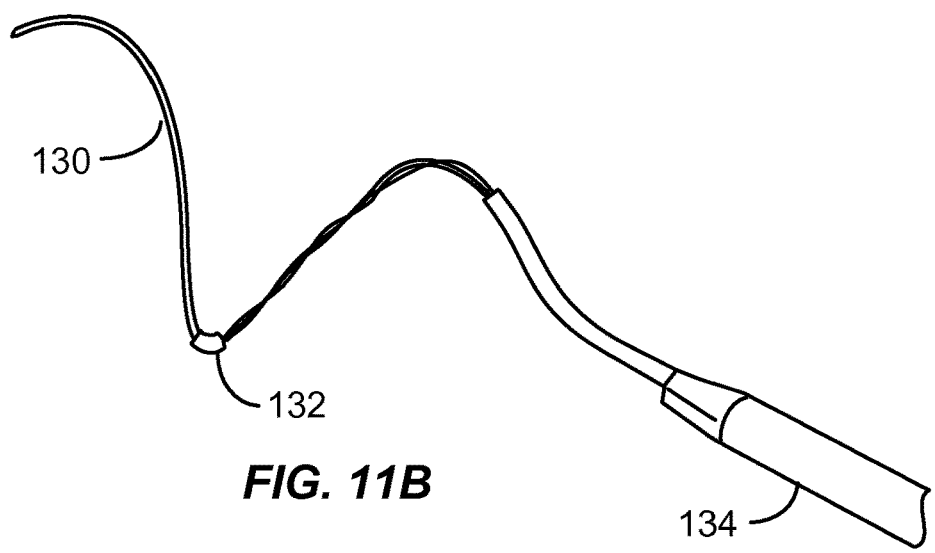
Figure 11C:
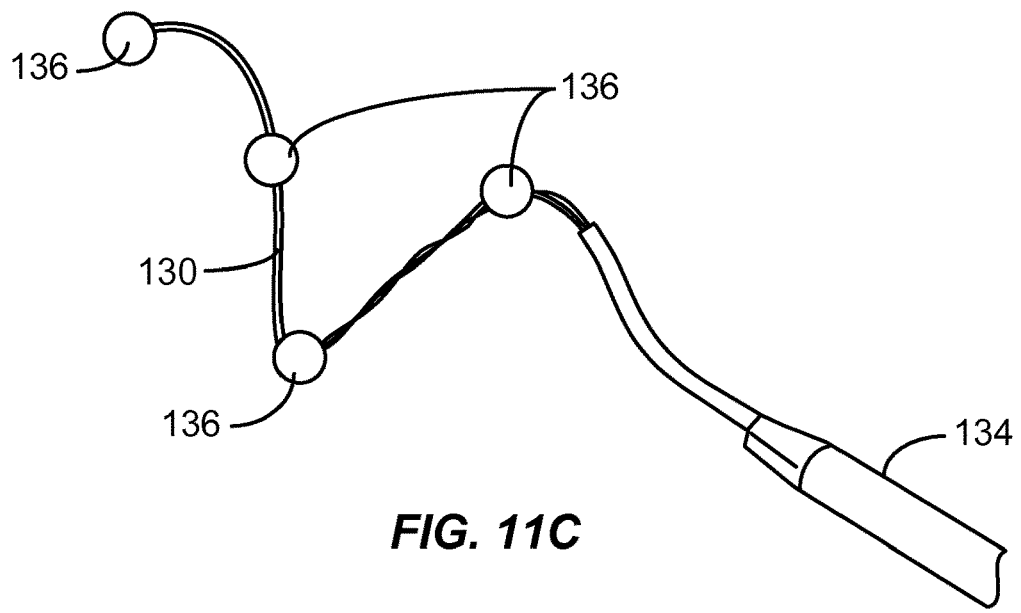

In another embodiment (FIG. 11A-11C), a straight Nitinol® or other superelastic wire 130 or other conductor is heat set into a helical shape at its distal end. An introducer catheter 134 carries the wire and is configured to be advanced to the renal pelvis, typically through the ureter. The wire 130 is then advanced from the lumen of the catheter. As it exits the catheter, the wire 130 assumes a pre-set helical shape. Application of RF through this wire will create a helical lesion in the renal pelvis. A thermocouple 132 may be secured to the wire for temperature measurement. The diameter of the catheter is 7 Fr-11 Fr. The diameter of the helix wire is 8 mm-20 mm in the free-state. The length of the helix is 8 mm-20 mm in the free-state. The diameter of the Nitinol® wire is in the ranges set forth above. In the embodiment of FIG. 11A-B, the helical wire is insulated at certain intervals to create a non-continuous, helical lesion pattern. In the embodiment of FIG. 11C, conductive contact pads 136 (e.g., metallic balls) are attached to the helical wire at specific intervals to enhance tissue contact and create non-continuous lesion patterns. The wire is insulated between the contact pads so that only the contact pads conduct energy to the tissue. Thermocouples are secured inside or proximate to one or more of the contact pads for temperature measurement. The diameter of the contact ball electrodes are in the ranges set forth above.

In another embodiment (FIGS. 12A-12C), a Nitinol® or other superelastic wire 140 or conductor is heat set into a helical shape. The wire is connected to the distal tip of an inner shaft 142 and the distal tip of an outer shaft 146. The inner shaft 142 fits and slides within a lumen of the outer shaft 146. When the inner shaft is extended, the wire is collapsed. When the inner shaft is retracted, the wire opens up into a helical shape. Application of RF through this wire will create a helical lesion in the renal pelvis. A thermocouple (not shown) may be secured to the wire for temperature measurement. The diameter of the outer shaft is 7 Fr-11 Fr. The diameter of the helix wire is 8 mm-20 mm in the expanded state (FIG. 12B). The length of the helix is 8 mm-20 mm in the expanded state. The diameter of the Nitinol® wire is 0.004 in to 0.025 in.

Figure 12A:
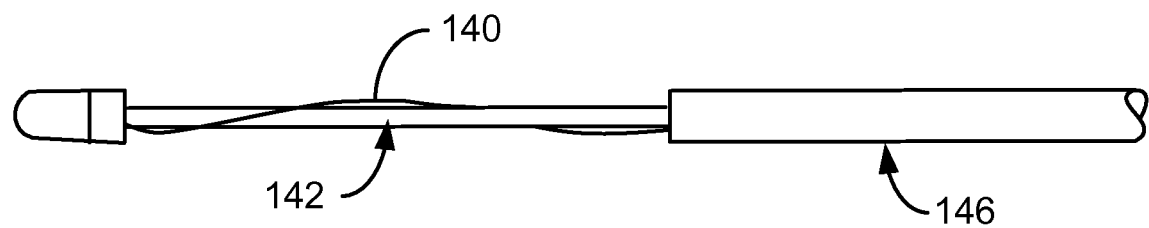
FIGS. 12A-12C illustrate a further alternative device configured to create deeper lesions in the renal pelvic wall.
Figure 12B:
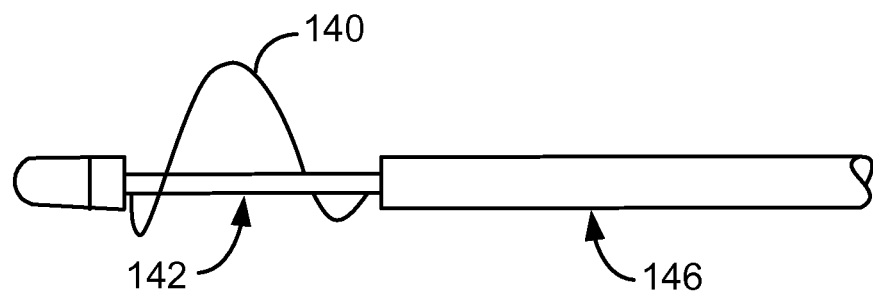
Figure 12C:
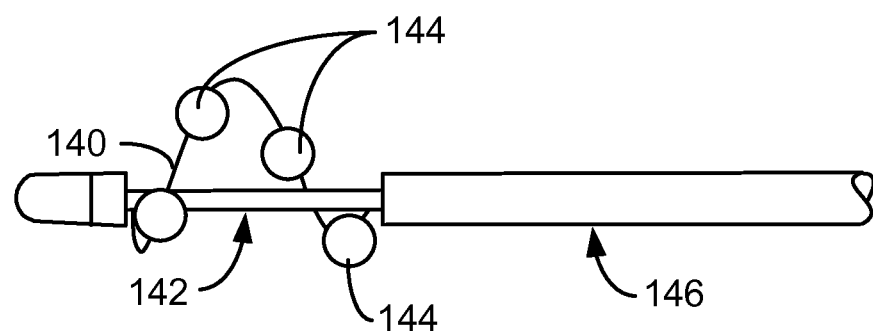

In the embodiment of FIGS. 12A and 12B, the helical wire is typically insulated at certain intervals to create a non-continuous, helical lesion pattern. In the embodiment of FIG. 12C, conductive contact pads 144 (e.g., metallic balls) are applied to the helical wire at specific intervals to enhance tissue contact and create non-continuous lesion patterns. The wire is insulated between the contact pads so that only the contact pads conduct energy to the tissue. Thermocouples are secured inside or proximate to one or more of the contact pads for temperature measurement. The diameter of the contact balls are 0.03 in-0.10 in.

Figure 13:
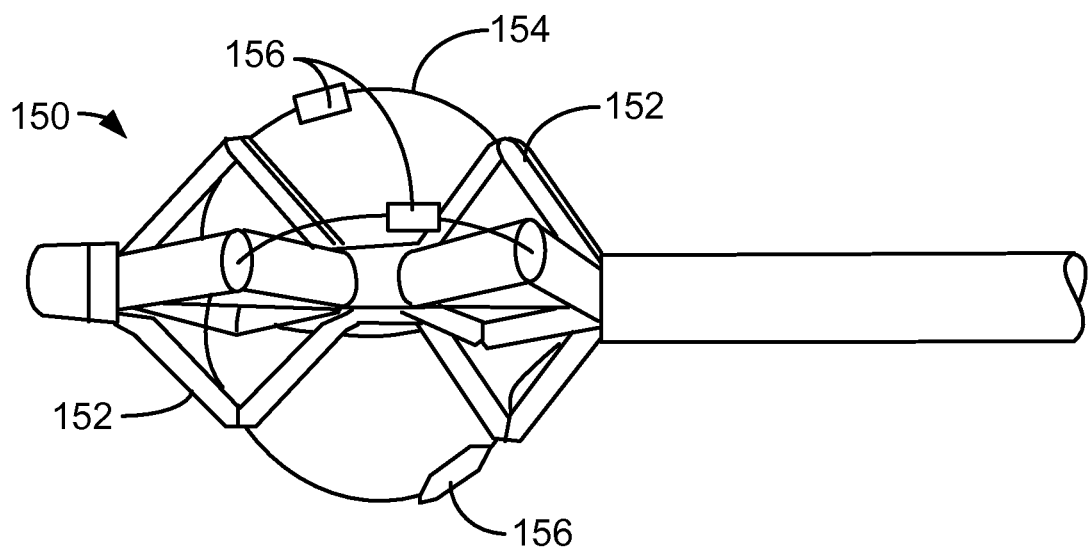
FIG. 13 illustrates a device where the wires carried by malecots have contact pads arranged in a helical pattern.

The device 150 of FIG. 13 includes two malecot supports 152. Wires 154 connect each of the eight ridges or peaks of the malecots, and each of the four wires is insulated except where a larger metallic contact pad 156 is secured. The contact pads are positioned so as to create a helical lesion pattern. Thermocouple(s) (not shown) may be placed on or proximate to one or more of the contact pads for temperature measurement. Wire diameter is 0.004 in to 0.01 5 in. Length and diameter of the malecots when expanded are typically from 8 mm-15 mm.

Figure 14A:
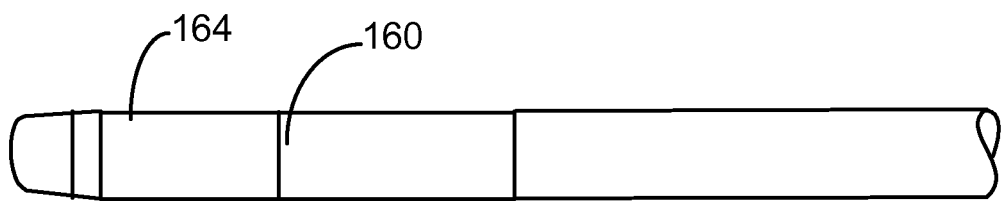
FIGS. 14A and 14B illustrates further alternative devices with deployable tine electrodes arranged in a helical pattern.
Figure 14B:
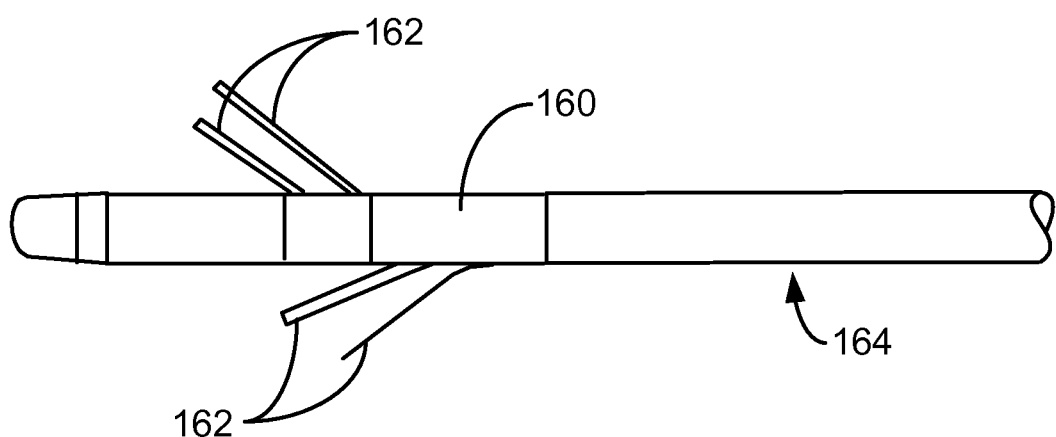

In another embodiment as illustrated in FIGS. 14A and 14B, a Nitinol® or other superelastic tube 160 is laser cut and heat set to form a plurality of outwardly biased tines 162. The tines are axially offset to create a helical pattern, and the tube 160 is electrically insulated except for the distal ends of the tines. The tube is secured to a catheter shaft (not shown), and a sheath 164 slides over the tube and catheter. As the sheath is slid distally, the tines are exposed and allowed to expand outward to contact the tissue. Application of RF energy will create discrete lesions in a helical pattern. Thermocouples (not shown) may be secured to the inside of one or more of the tines for temperature measurement. The sheath diameter is 7 Fr to 11 Fr. The tips of the tines expand to create a helix with a diameter of 8 mm-20 mm.

Figure 15:
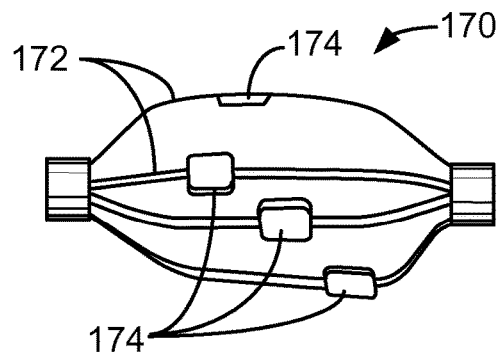
FIG. 15 illustrates another self-expanding support structure carrying a helical arrangement of electrode contact pads.
Figure 20:
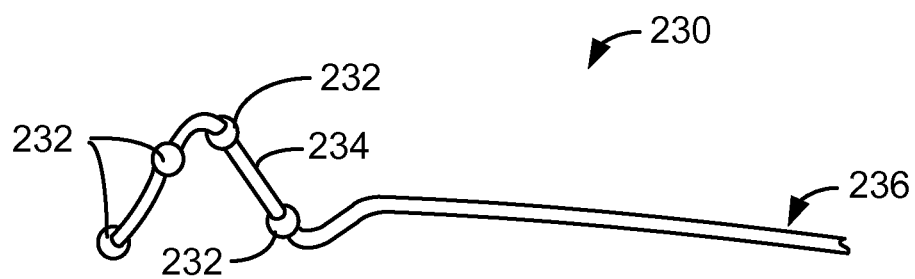
FIGS. 20-23 illustrate a renal wall ablation device similar to that of FIGS. 11A-11C.
Figure 21:

In yet another embodiment (FIG. 15), a Nitinol® or other superelastic tube is laser cut and heat set so as to create a self-expanding bulb 170 with a plurality of struts 172 which carry contact pads 174. The tube is electrically insulated, except for the contact pads. FIG. 20 shows the laser cut tube only, but the tube would be secured to a catheter shaft (similar to any of the catheter shafts shown previously) at a proximal end of the tube. A sheath is slid over the tube to contract the bulb. As the sheath is slid proximally, the bulb opens and the contact pads expand to contact the tissue. Thermocouples may be secured to the inside of one or more of the tines for temperature measurement. Application of RF energy will create discrete lesions in a helical pattern. The sheath diameter is 7 Fr to 11 Fr, and the bulb expands to a diameter of 8 mm to 20 mm.

In still other embodiments, a single ball-electrode may be disposed at the distal end of a steerable catheter and may be used to create discrete lesions one-at-a-time. The user positions the ball to contact the tissue at the appropriate spots. The electrode can be monopolar or bipolar. A thermocouple may be secured inside or proximate to the ball for temperature measurement. The ball diameter is typically 0.02 in-0.10 in.

As an alternative to targeting the nerves embedded close to the surface the wall of the renal pelvis, it may be advantageous to target the nerves further away from the renal pelvic wall (e.g., nerves surrounding the renal arteries). The inventors herein have found that damaging the wall of the renal pelvis may be detrimental to proper function. Therefore, in these other embodiments, it would be advantageous to target nerves farther away from the renal pelvic wall, while leaving the renal pelvic wall intact. In addition, it would be advantageous to do this by accessing the renal pelvis, or anywhere along the ureter or kidney. Previously described ultrasound catheters deliver acoustic energy "to heat the wall of the renal pelvis and renal nerves embedded in the tissue bed surrounding the renal blood vessels". This achieves reaching the farther nerves. In order to lessen risk of damaging the renal pelvic wall, the present invention can employ "focused" ultrasound transducers (high intensity focused ultrasound or HIFU) which can directly heat tissue surrounding the target nerves with minimal heating of the pelvic wall and the tissues immediately adjacent to the pelvic wall. Thus, an ultrasonic transducer catheter can access the renal pelvis through the ureter and deliver energy to tissue beyond the renal pelvic wall while keeping the renal pelvic wall intact with minimal heating.

Catheters according to the present invention may comprise tissue-penetrating elements in addition to the radiation-emitting elements which have been previously described. For example, the tissue-penetrating elements may comprise radio frequency electrodes, chemical delivery structures, heat delivery structures, cryogenic delivery structured, and the like.

The devices described above are mainly intended for transuretheral approaches. Most of these designs, however, are also suitable for a vascular approach where the renal nerves are targeted by passing a catheter through the renal artery and creating lesions through the artery. Current vascular approach renal denervation devices typically create helical lesions. Thus, all of the above designs that create helical lesions can be adapted for the vascular approach. Catheter sizes for such a vascular approach are in the range from 4 Fr to 8 Fr.

Figure 16:
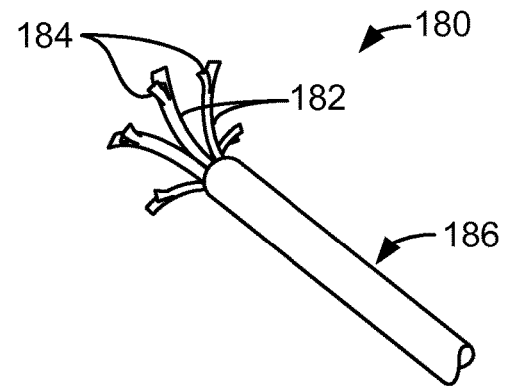
FIGS. 16-19 illustrate tools configure to mechanically disrupt nerves in the renal pelvis wall.

The renal nerve pathways may also be disrupted by mechanical means. In one embodiment, as illustrated in FIG. 16, an expandable member 180 is formed from a laser cut Nitinol® or other superelastic tube that is heat set with expandable tines 182 and bent up tabs 184 that act as cutters. A sheath 186 may be advanced to collapse the tines inside the sheath. When the sheath is retracted, the tines self-expand outwardly so that the cutters can contact with the wall of the renal pelvis. The device is then rotated and/or translated axially so as to scrape the inner wall of the renal pelvis. This scraping will disrupt the nerves at the surface of the renal pelvis wall. In order to control bleeding, a balloon can be inserted into the renal pelvis after the scraping to apply pressure to the walls. The sheath size for this device is 7 Fr to 11 Fr. Various other embodiments for mechanical renal denervation can also be used including a single scraper consisting of a curved member with a sharp distal area and an expandable stent-like device with various sharp areas.

Figure 17:
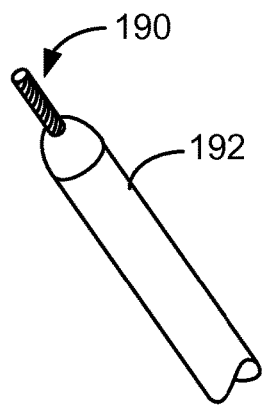

In another embodiment, as shown in FIG. 17, mechanical denervation may be done using high frequency vibration. High frequency vibration has been used in other medical devices for such purposes as tunneling and boring. In this embodiment, a tip or "effector" 190 may have various geometries, may be delivered via a catheter 192, and may be placed on the urothelium of the renal pelvis where it is driven by a generator such as a piezoelectric or other transducer to provide high (>1000 Hz) or low (<1000 Hz) frequency energy where the resulting vibration for causes scraping and/or abrading of the surface of the urothelium to disrupt nerves. The tip 190 may be retractable in the catheter 192. Such vibratory catheters will typically be sized from 7 Fr to 11 Fr. Other suitable effector geometries may include but are not limited to (1) rectangular, flat surface area, (2) helical surface area, (3) effector of curved geometry for enhanced contact with the renal pelvis, and (4) steerable effector for targeted contact with the renal pelvis.

Figure 18:
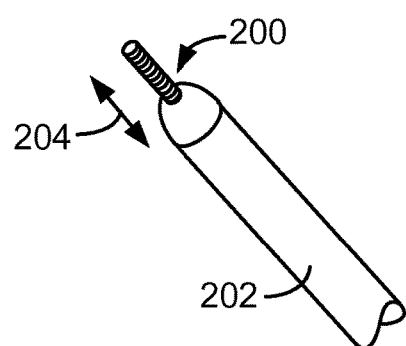

In still another embodiment as illustrated in FIG. 18, mechanical denervation may be accomplished via a reciprocating motion. A shaft 200 is reciprocated axially (the direction of arrow 204) within a larger catheter shaft 202 and can abrade the surface of the renal pelvis. An inner telescopic shaft may be knurled or of similar geometry to cause abrasion for the purpose of denervation. Such reciprocating-element catheters will typically be sized from 7 Fr to 11 Fr. Other suitable shaft geometries include but are not limited to (1) a shaft tip with curved geometry for enhanced contact with the renal pelvis, and (2) a steerable tip for targeted contact with the urothelium of the renal pelvis.

Figure 19:
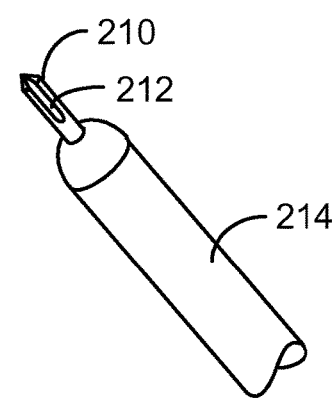

Mechanical denervation may also be accomplished using tools similar to those used for tissue biopsy, as shown in FIG. 19. Such tool would include a needle element 210 having a groove 212. The needle would reciprocate from a catheter 214 and be used to remove small amounts of the renal pelvis in strategic locations. Many biopsy devices exist for various parts of the body. This embodiment, however, would be specific to the renal pelvis and for the purposes of excising small portions of the pelvis layers in an effort to capture and disrupt renal nerves. The catheter size for this device is 7 to 11 Fr. Various other biopsy geometries and elements may include but are not limited to (1) a cannulated sheath to cover the needle tip with our without circumferential rotation for the purposes of aiding tissue excising, (2) a curved geometry for enhanced contact with the renal pelvis, and (3) a steerable device for targeted contact with the renal pelvis.

Referring now to FIGS. 20-23, a device 230 for deploying helically disposed ball electrodes 232 on a pre-shaped wire 234 will be described. The wire 234 may be a superelastic Nitinol® wire having a distal end that is set into a helical or spiral shape. The plurality of metal balls 232 (four being illustrated in the drawings but anywhere from two to ten typically being useful) are attached to the wire 234 and heat shrink tubing 236 is placed over a proximal length of the wire and between the balls for insulation. A thermocouple may be attached to the most proximal ball. The Nitinol® wire diameter is typically 0.4 mm. The ball diameter is typically 12 mm. When the insulation is applied over the wire, it typically has a wall thickness of 0.1 mm and an outer diameter of typically 0.6 mm. A smaller wall thickness can be obtained by replacing the heat shrink tubing with a dielectric coating. The helical pitch is typically 12 mm. The pitch diameter (through the center of the wire) is typically 0.8 mm. The wire will be delivered through a sheath 238 which is steerable at the distal end, either being shapeable or pre-shaped. The sheath typically has an inner diameter of 2.1 mm and an outer diameter of 2.6 mm.

Figure 24:
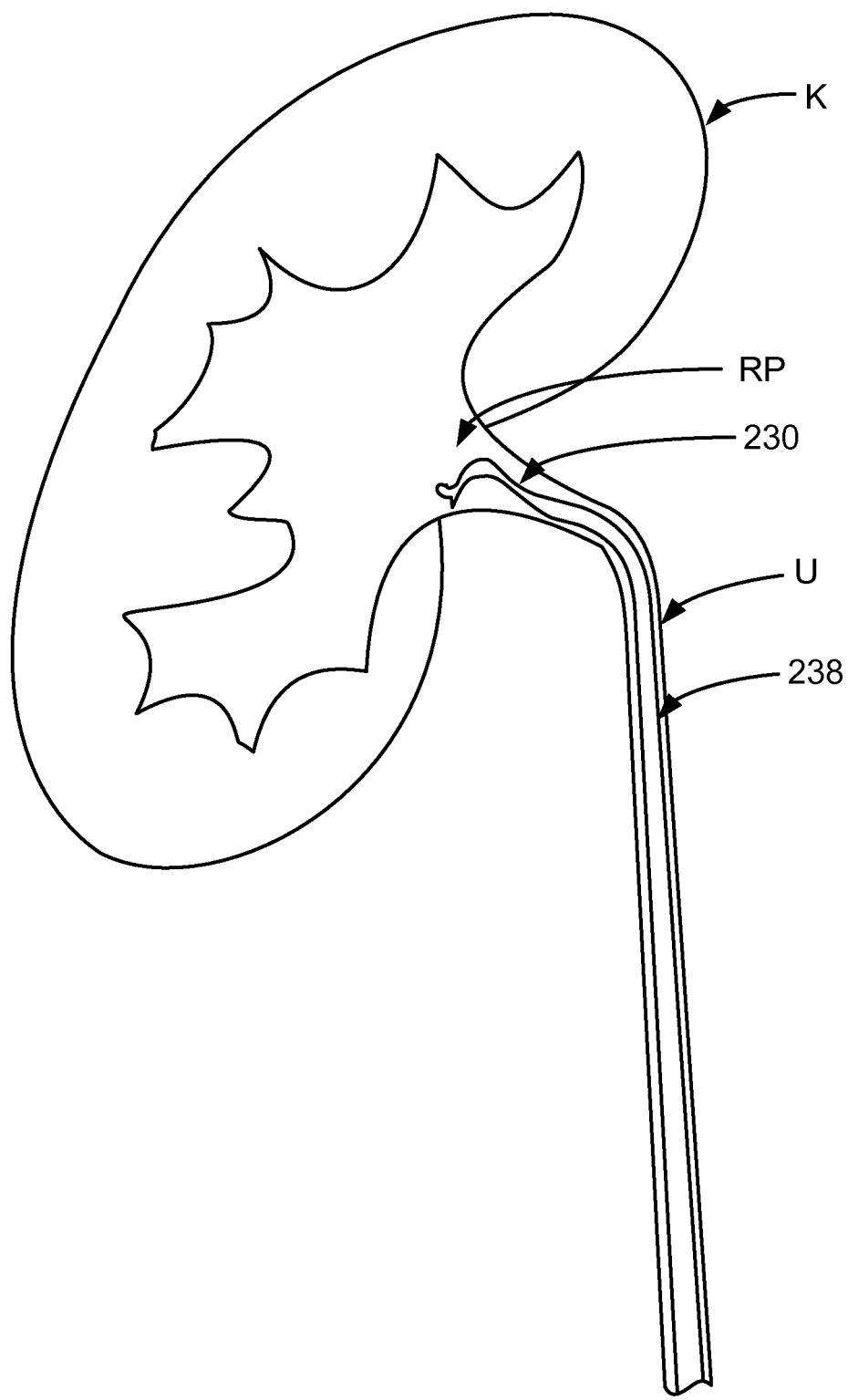
FIG. 24 illustrates use of the device of FIGS. 20-23 in ablating a renal pelvis wall.

The device 230 may be delivered to the renal pelvis RP as shown in FIG. 24. A guidewire (not shown) is first passed through the urethra, into the bladder, into the ureter U, and up to the kidney K. A dilator (not shown) is placed into the center lumen of the sheath 238. The dilator and sheath are then threaded up the guidewire into ureter and positioned so that the distal end of the sheath is just proximal of the renal pelvis. The guidewire and dilator are then removed, leaving just the sheath in place. The device 230 is then inserted through the sheath until the helical portion exits the distal end. The sheath can then be steered to position the device in the center of the renal pelvis. RF energy is then applied to the device and lesions are created at the ball/tissue interface.

In alternative configurations, each ball electrode can be independently turned on/off. A separate thermocouple can be fixed to each ball to monitor independent ball temperatures. The electrodes/wire can be stamped as shown in the Figure. These designs can be scaled down for renal denervation through the renal artery instead of through the renal pelvis.

Figure 25:
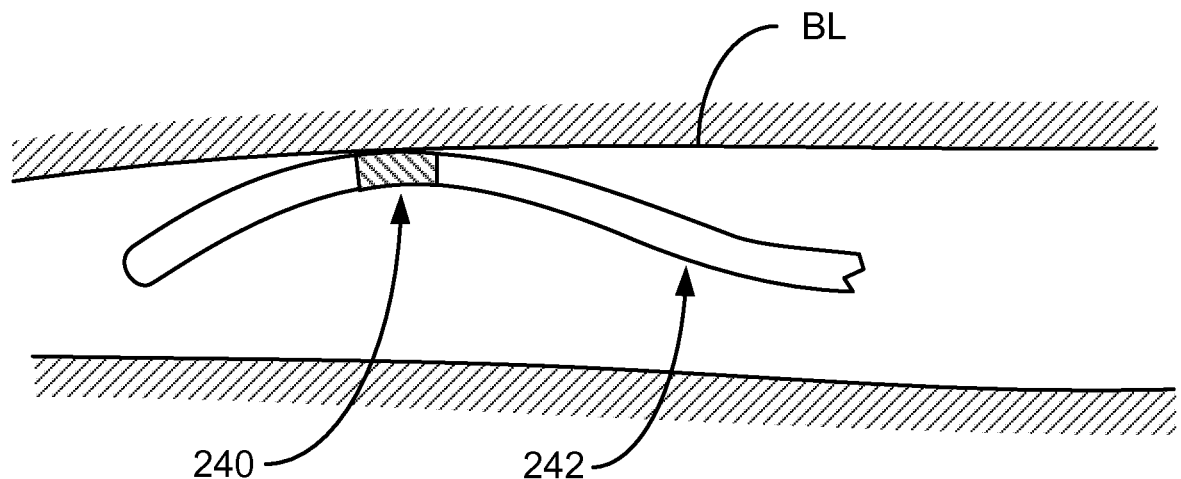
FIGS. 25 and 26 illustrate the use of device with cylindrical electrodes and spherical electrodes for ablating a luminal wall.
Figure 26:
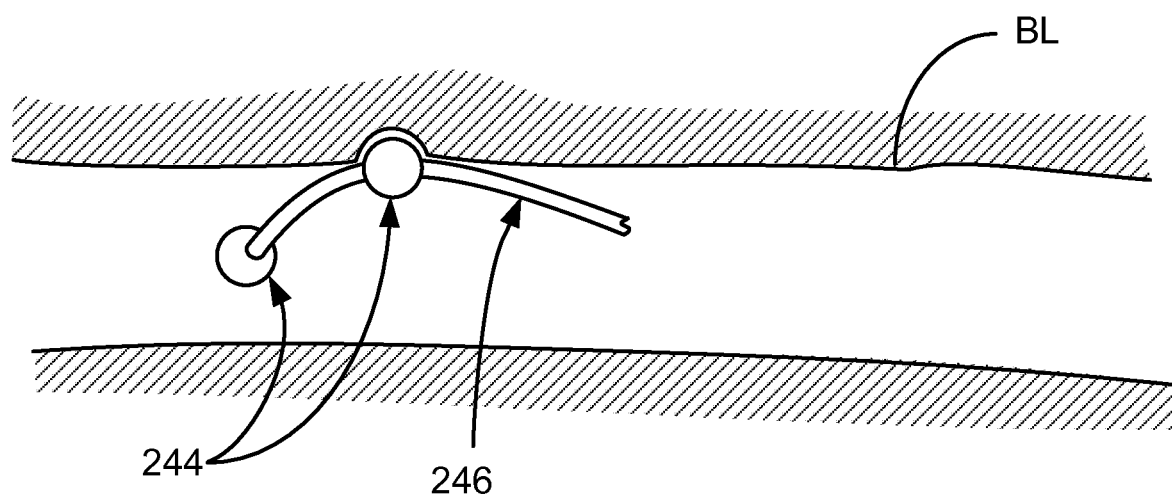

As shown in FIGS. 25 and 26, a cylindrical or "band" electrode 240 carried on a catheter or wire 252 will have only moderate contact with the wall of a body lumen BL. A relatively large ball electrode 244, however, carried on a smaller wire 246, will embed into the wall and provide a much greater surface contact area with the wall of the body lumen BL than a conventional band electrode.

As shown in FIGS. 27A-27C, a vacuum can be applied inside the ureter and/or renal pelvis to collapse the walls of the kidney. This technique can be very useful to help bring the tissue throughout the renal pelvis into intimate and conforming contact with electrodes and other mechanical effectors, as shown for example in FIG. 27C. All devices described herein can benefit from such vacuum application and kidney wall collapse, but most if not all of the devices can function with no or only a partial collapse. This vacuum-assisted approach is not intended to be applied to vascular renal denervation approaches As shown in FIG. 27A, an ablation device 300 comprises a Nitinol® or other superelastic nickel-titanium alloy wire 302 with ball electrodes 304 attached. When deployed through a catheter 306 into the renal pelvis RP, the wire takes on a shape similar to pelvis. The assumed shape typically occupies a three-dimensional within the renal pelvis to help engage or approximate balls against the tissue surface of the inner renal pelvic wall. Vacuum is applied, typically through a lumen of the catheter 306 to help embed the balls into tissue surface. RF energy is applied through the wire to the balls to create discrete lesions, damaging the renal nerves. The wire can optionally be pre-shaped in order to approximate the shape of the pyramids surrounding the renal pelvis.

Figure 28A:
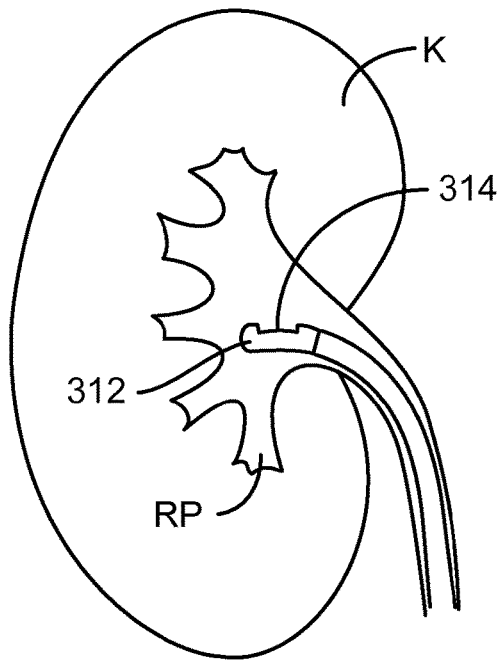
FIGS. 28A-28C show a catheter with a cutting blade inside the renal pelvis.
Figure 28B:
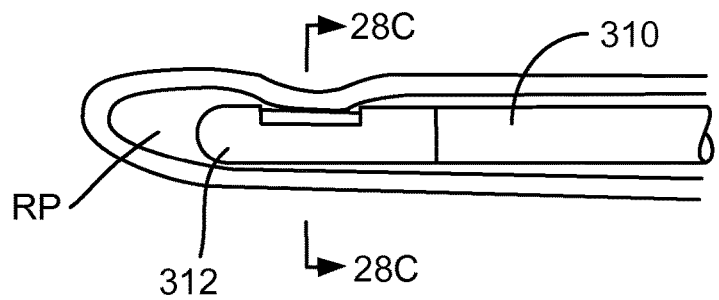
Figure 28C:
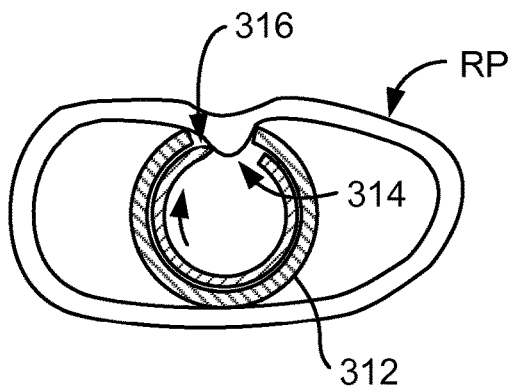

As shown in FIGS. 28A-28C, a mechanical cutter 312 is attached to a distal end of a catheter 310 having a cutting slot 314. A vacuum may be applied to draw tissue into the cutter slot 314 and a cylindrical blade 316 may be rotated to excise a small piece of tissue. Removal of renal pelvic tissue in this manner will sever renal nerves.

Figure 29A:
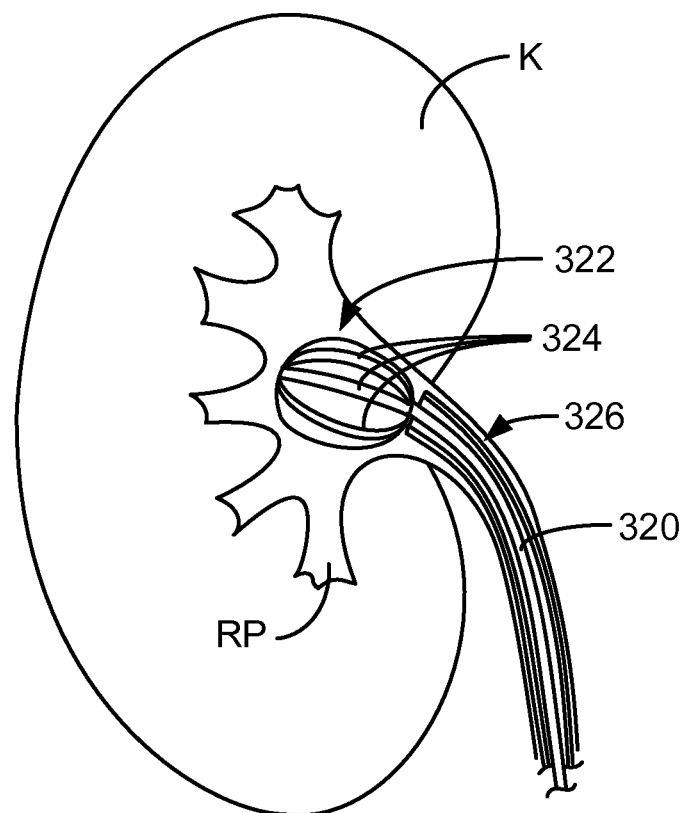
FIGS. 29A and 29B show a balloon with abrasive strips attached to the outsides deployed inside the renal pelvis.
Figure 29B:
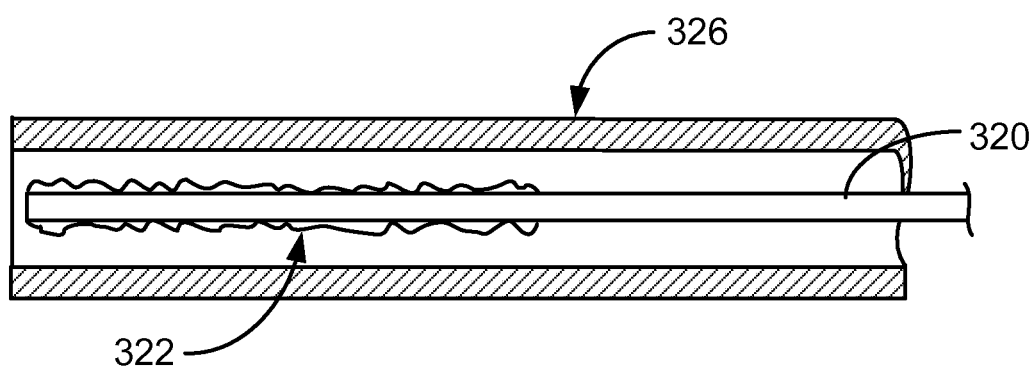

As shown in FIGS. 29A and 29B, a catheter 320 carries a distal balloon 322 having a plurality of abrasive strip 324 thereon. The balloon on the catheter may be deployed into the renal pelvis RP and, once inside the renal pelvis, a vacuum is optionally drawn and the balloon is rotated and/or translated to abrade the tissue surface. Such abrasion damages the renal nerves.

Figure 30A:
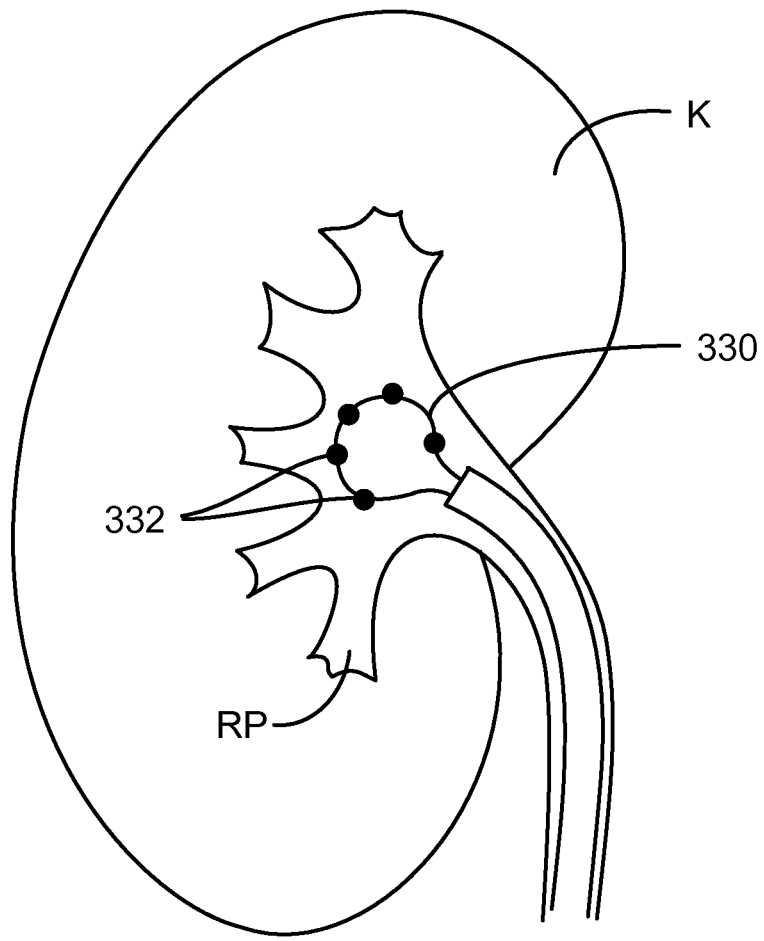
FIGS. 30A and 30B show a superelastic alloy loop wire with abrasive balls attached to the distal end.
Figure 30B:
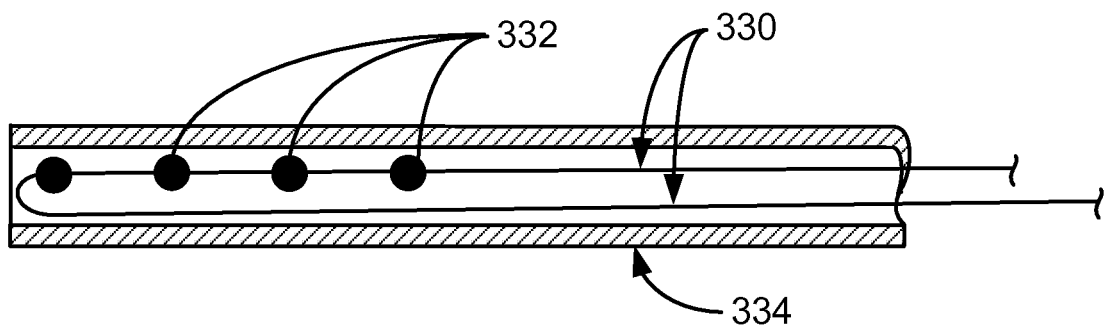

As shown in FIGS. 30A and 30B, a Nitinol® or other elastic wire 330 carries a plurality of abrasive balls 332. The wire 330 is preferably formed into a loop structure so that it expands across the renal pelvis when it is advanced from a delivery sheath or catheter 334. Once deployed, a vacuum is optionally applied, and the wire loop and balls are rotated and/or translated to abrade the tissue surface. This abrading damages the renal nerves.

Figure 31A:
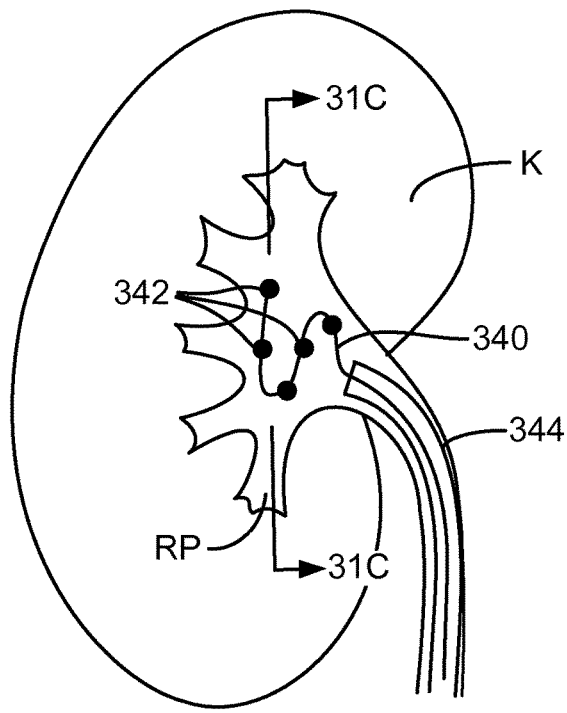
FIGS. 31A-31C show ball electrodes on a superelastic alloy wire deployed out of a sheath and into the renal pelvis where the wire takes on a serpentine shape.
Figure 31B:
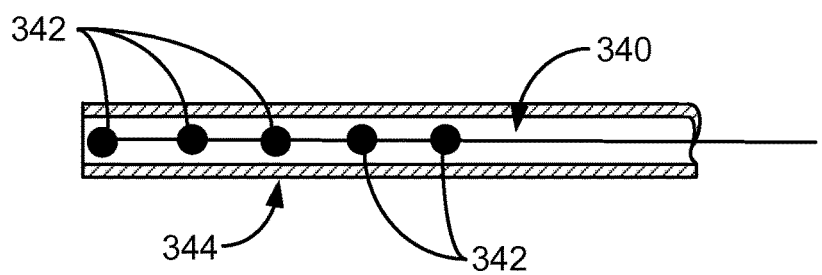
Figure 31C:
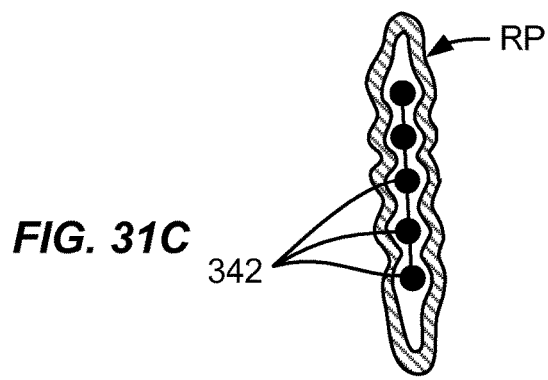

As shown in FIGS. 31A-31C, a Nitinol® or other elastic wire 340 carries a plurality of ball electrode 342. When deployed into the renal pelvis RP, the wire 340 is pre-shaped to assume a two-dimensional serpentine shape. Vacuum is optionally applied to help embed the electrode balls into tissue surface. RF energy is applied through the wire to the balls to create discrete lesions, thus damaging the renal nerves. Alternatively, the wire shape can be pre-shaped in a circular, semi-circular, linear, spiral, or any other geometry with proximal and distal ends.

Figure 32A:
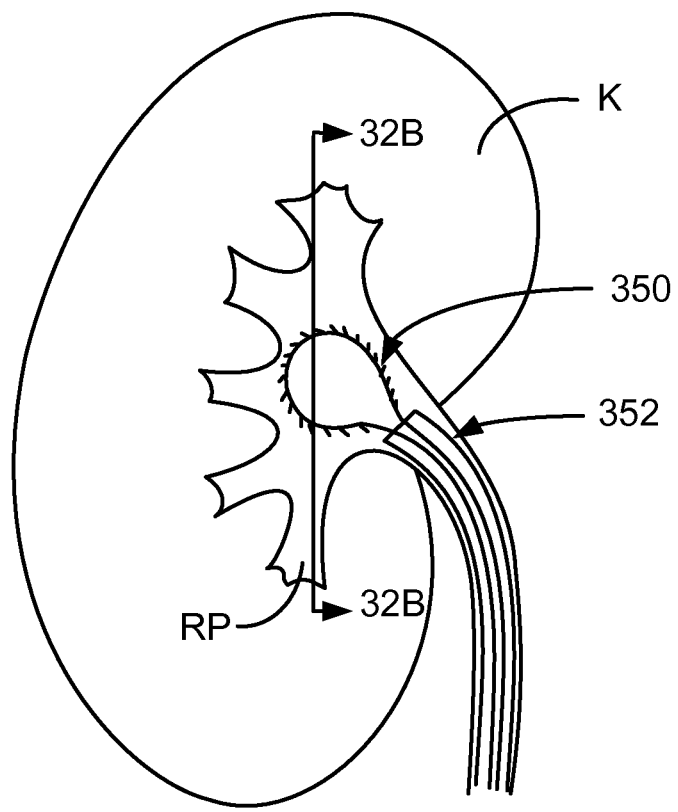
FIGS. 32A and 32B show a saw-tooth wire loop both inside a sheath and deployed in the renal pelvis.
Figure 32B:
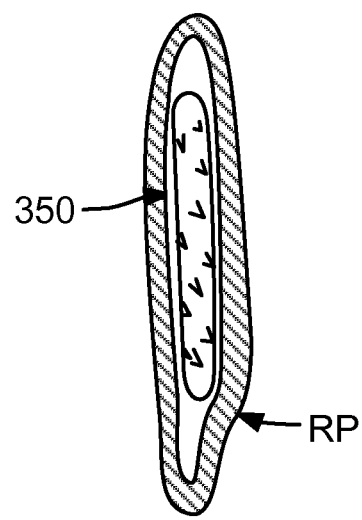

As shown in FIGS. 32A and 32B, a Nitinol® or other elastic wire 350 is formed with saw-teeth and deployed from a catheter or sheath 352 into the renal pelvis RPs. Once deployed, the saw-tooth wire can be translated and/or rotated to cut and/or abrade the tissue lining the inner wall of the renal pelvis. Applying a vacuum to the renal pelvis will help to keep the tissue in contact with the wire. This cutting/abrading damages the renal nerves.

Figure 33C:
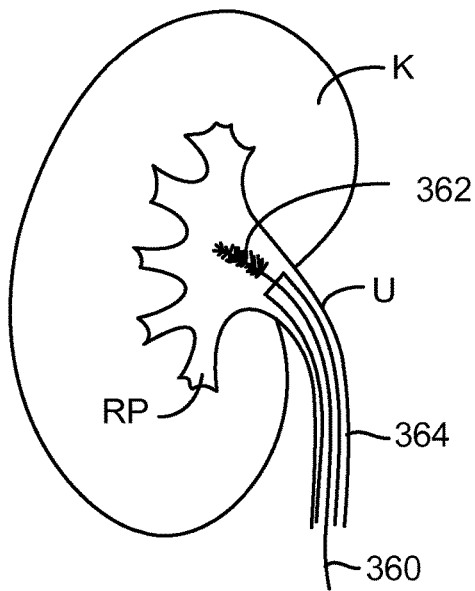
FIGS. 33A-33D show a wire brush and balloon tamponade both inside a sheath and deployed in the renal pelvis.
Figure 33A:
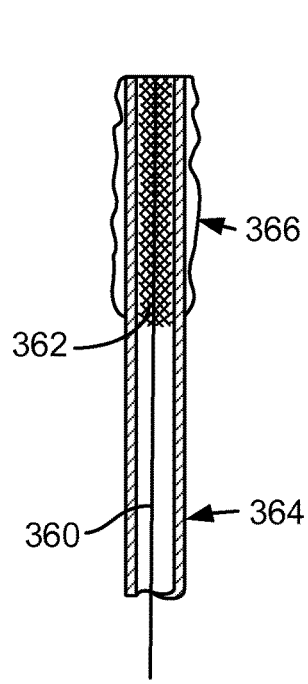
Figure 33B:
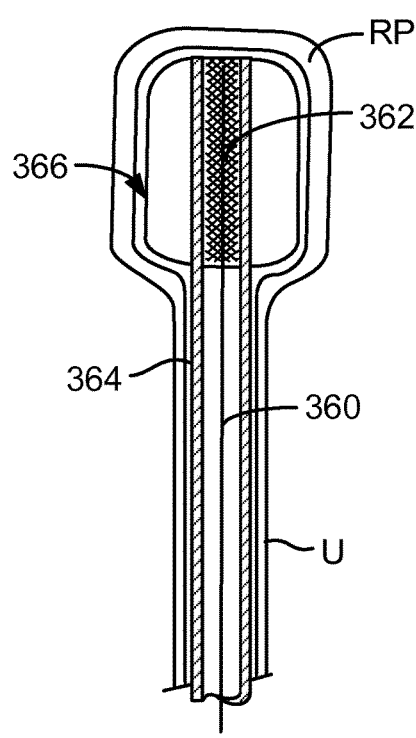
Figure 33D:
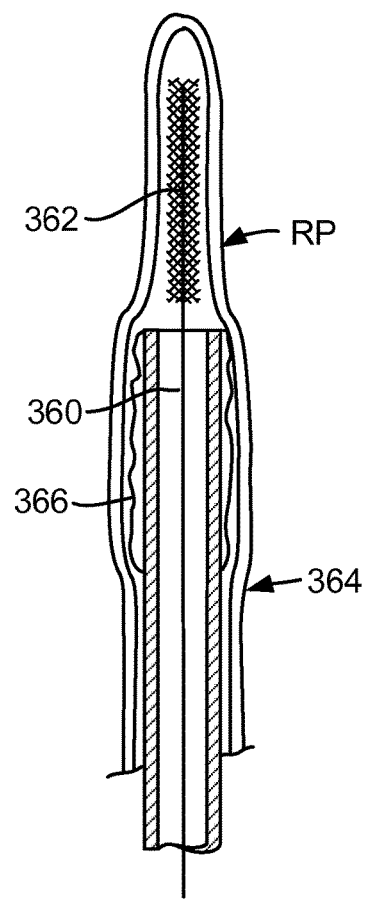

As shown in FIGS. 33A-33D, a Nitinol® or other elastic wire 360 carries a wire brush 362 which in turn is carried within a lumen of a catheter 364 having a distal balloon 366. The brush 362 is deployed from the ureter U into the renal pelvis RP, as shown in FIGS. 33B and 33C. The brush is then rotated and/or translated to abrade the tissue surface. A vacuum can be applied to help keep the tissue in contact with the brush. This abrading damages the renal nerves. After abrading, the brush is returned to the inside of the catheter. The balloon is then deployed inside the renal pelvis (FIG. 33D) to act as a tamponade and stop bleeding from the abraded tissue. The balloon may optionally have electrodes or other current delivery elements to apply electrocautery.

As shown in FIGS. 34A-34C, a catheter 370 carries a distal balloon 372 having a plurality of micro-spikes 374 thereon. The balloon on the catheter may be deployed into the renal pelvis RP and, once inside the renal pelvis, a vacuum may be drawn and the balloon will be inflated and rotated and/or translated to abrade the tissue surface. Such abrasion damages the renal nerves. The micro-spikes may optionally be hollow to deliver therapeutic or other agents to the wall of the renal pelvis either before, during, or after the abrasion. An exemplary agent is ethanol which will deactivate the nerves.

Figure 35A:
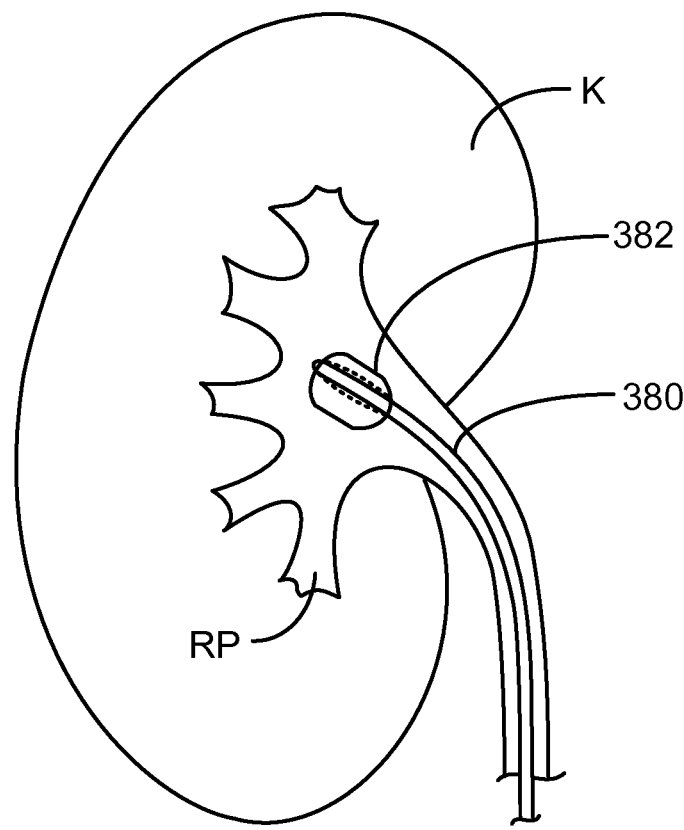
FIGS. 35A and 35B show a drug delivery balloon with openings on top and bottom sides to direct drug delivery to specific tissue areas.
Figure 35B:
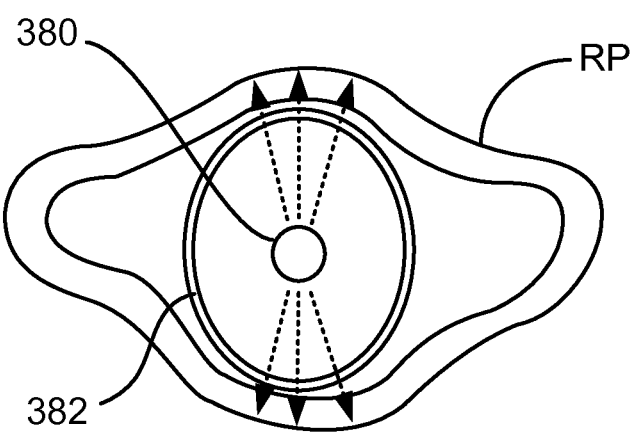

As shown in FIGS. 35A and 35B, a catheter 380 carries a distal balloon 382 having a plurality of infusion holes or ports thereon. The holes are typically deposed on the top and bottom of the balloon so that they will deliver substances directly into the wall of the renal pelvis RP, as shown in FIG. 35B. Preferably, a vacuum is applied to the renal pelvis to engage the holes against the tissue for targeted placement.

Figure 36A:
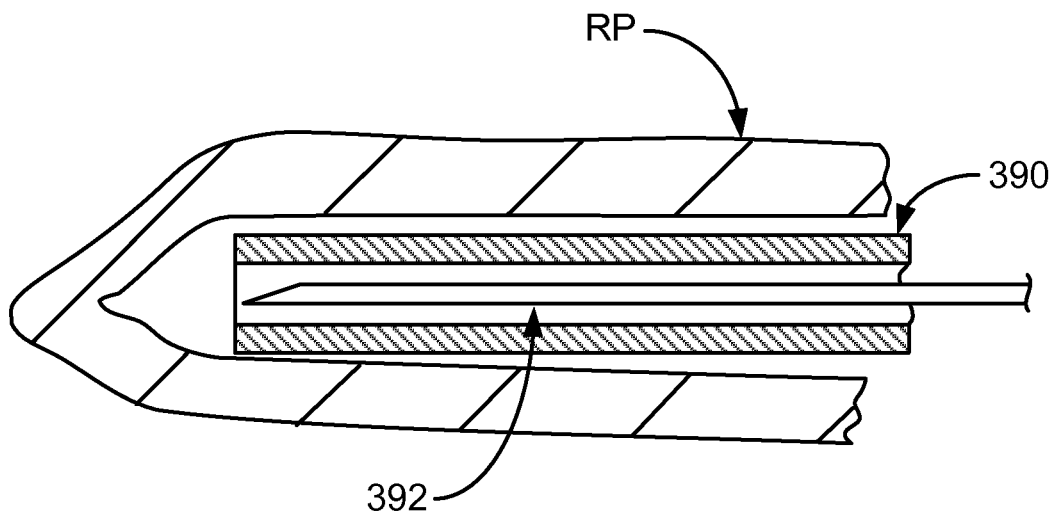
FIGS. 36A and 36B show a catheter with drug delivery needle both inside a sheath and deployed into the renal pelvic tissue.
Figure 36B:
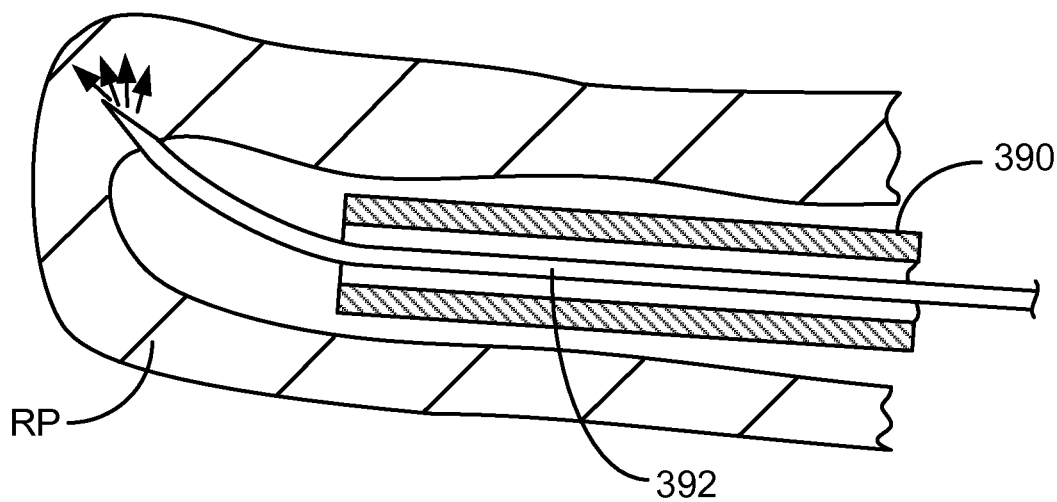

As shown in FIGS. 36A and 36B, a catheter 390 carries a deployable needle 392. The catheter is positioned inside the renal pelvis RP, and the needle is deployed, to pierce through the wall of the renal pelvis. Agents such as ethanol can then be delivered through the needle into the tissue to deactivate the renal nerves. Note that while the figures show the needle deploying from the distal tip of the catheter, the needle or a plurality of needles can alternatively exit through side holes in the catheter. A vacuum will preferably be used to approximate the tissue to the catheter and facilitate needle penetration.

Figure 37:
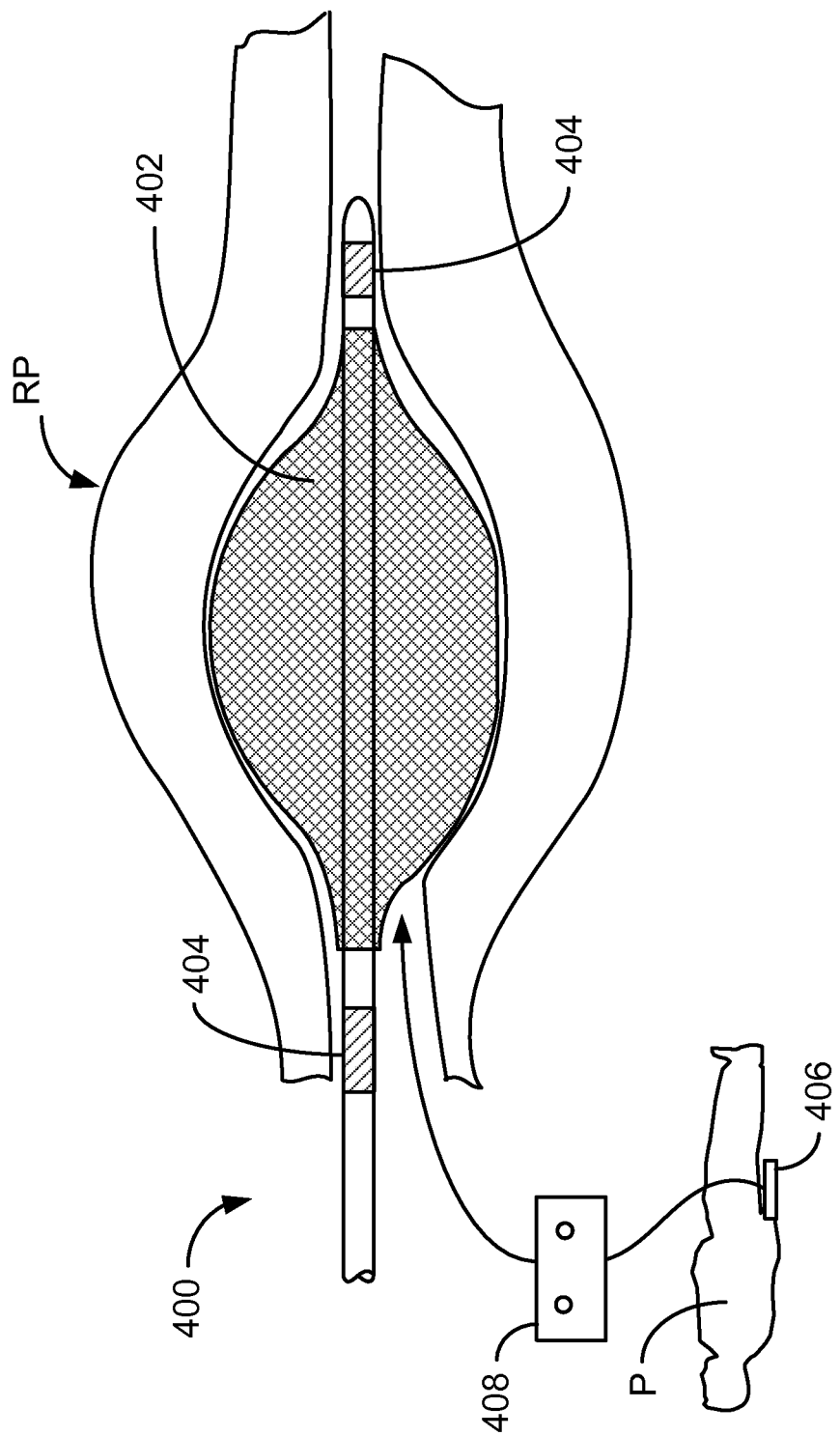
FIG. 37 shows a catheter system with expandable mesh for iontophoretic drug delivery.
Figure 39:
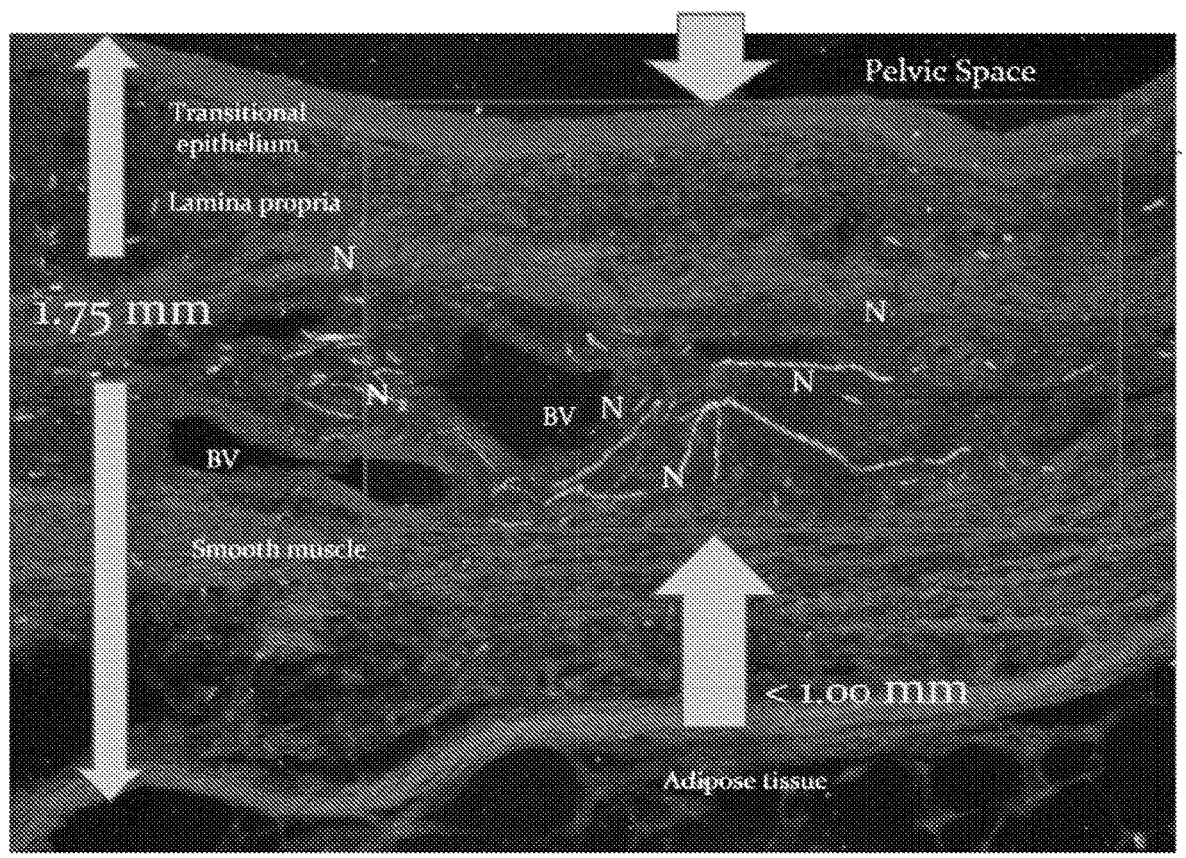
FIG. 39 shows a magnified cross section of renal pelvic tissue with the letter "N" illustrating nerves.
Figure 40:
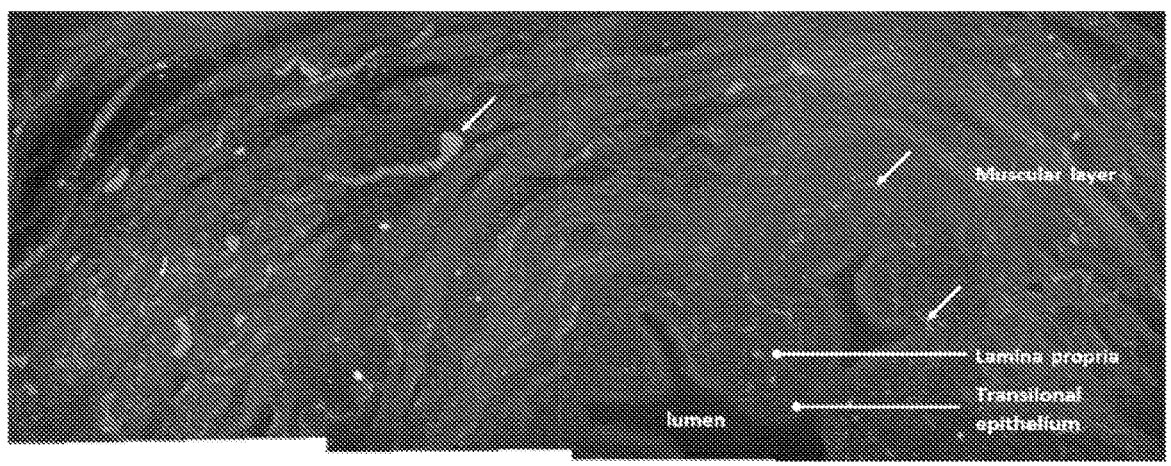
FIGS. 40-42 show magnified cross sections of ureteral tissue with arrows pointing to nerves.
Figure 41:
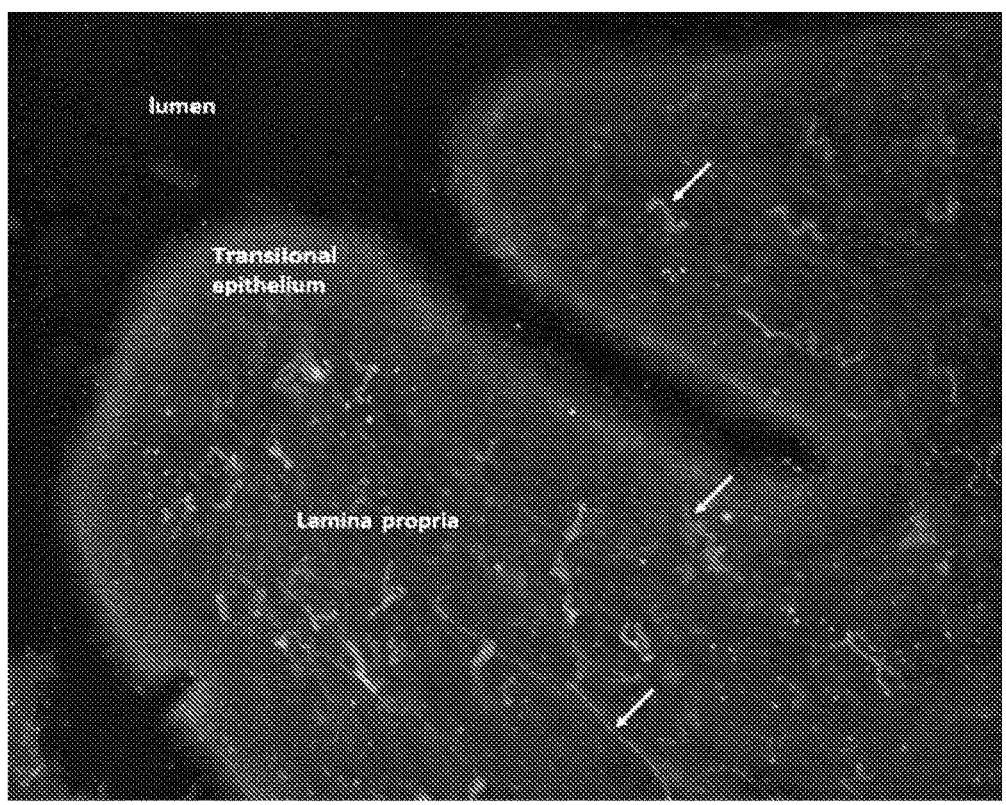
Figure 42:
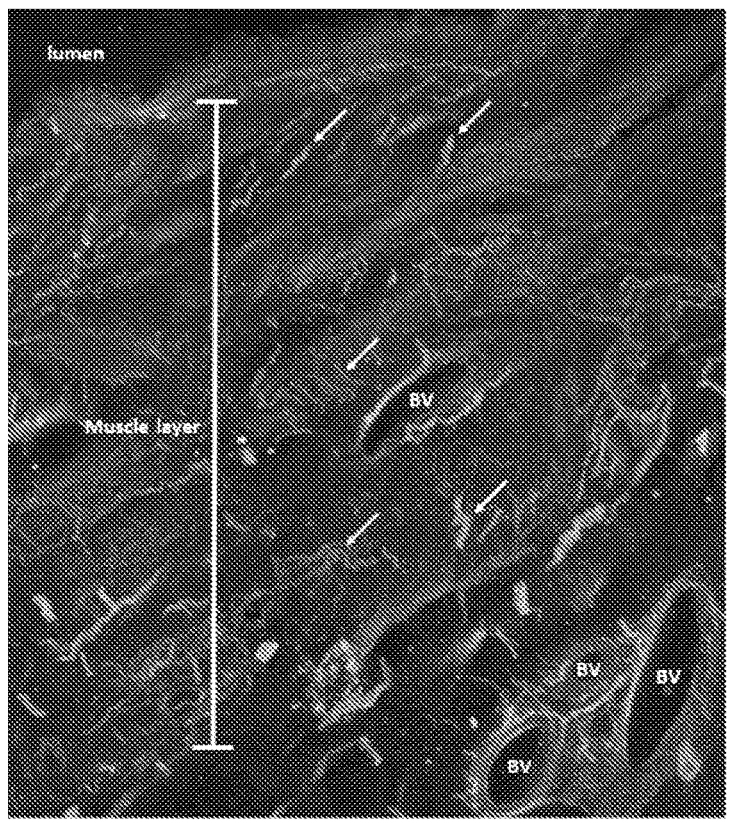

As shown in FIG. 37, an iontophoresis catheter 400 carries an electrically conductive, radially expansible cage 402 at its distal end. Iontophoresis is a physical process in which ions flow diffusively in a medium driven by an applied electric field. By applying an electrical potential, agents can be selectively absorbed by tissue. The electrically conductive, radially expansible cage 402 is radially expanded to contact the renal pelvis walls and acts as an anode. A nerve affecting agent can then be injected to the site and will be absorbed by the tissue at the mesh/tissue interface. The cathode can be provided by electrodes 404 on the catheter and/or an external cathode pad 406 on the patient's P skin. The cage and the cathodes are connected to a suitable power supply 408.

As shown in FIGS. 38A-38D, a balloon catheter 410 carries a balloon 412 covered by a sheath or jacket formed from a mesh covered by a silicone or other elastomeric material. Silicone sleeves are placed over the proximal and distal ends of the mesh layer. The catheter has a fluid lumen 414 with an exit port adjacent a proximal end of the silicone, between the silicone and the catheter and into the mesh. Fluid is passed through the fluid lumen and flows in between the strands of the mesh which sandwiched between the balloon and the silicone. The fluid then exits the distal end of the proximal silicone and contacts the tissue between the two silicone sleeves. This allows for targeted delivery for nerve affecting agents. This design can also be used in vascular catheters to deliver drugs to vessel walls.

FIGS. 39-42 are images obtained by the inventors showing the renal pelvic nerves to be within 1 mm of the tissue surface. The devices of the present invention are configured to particularly target this depth. As shown in FIGS. 38-42, the ureter is also rich with renal nerves. The devices of the present invention can also be configured to target nerves within the ureter in addition to or as an alternative to nerves in the renal pelvis.

Figure 43:
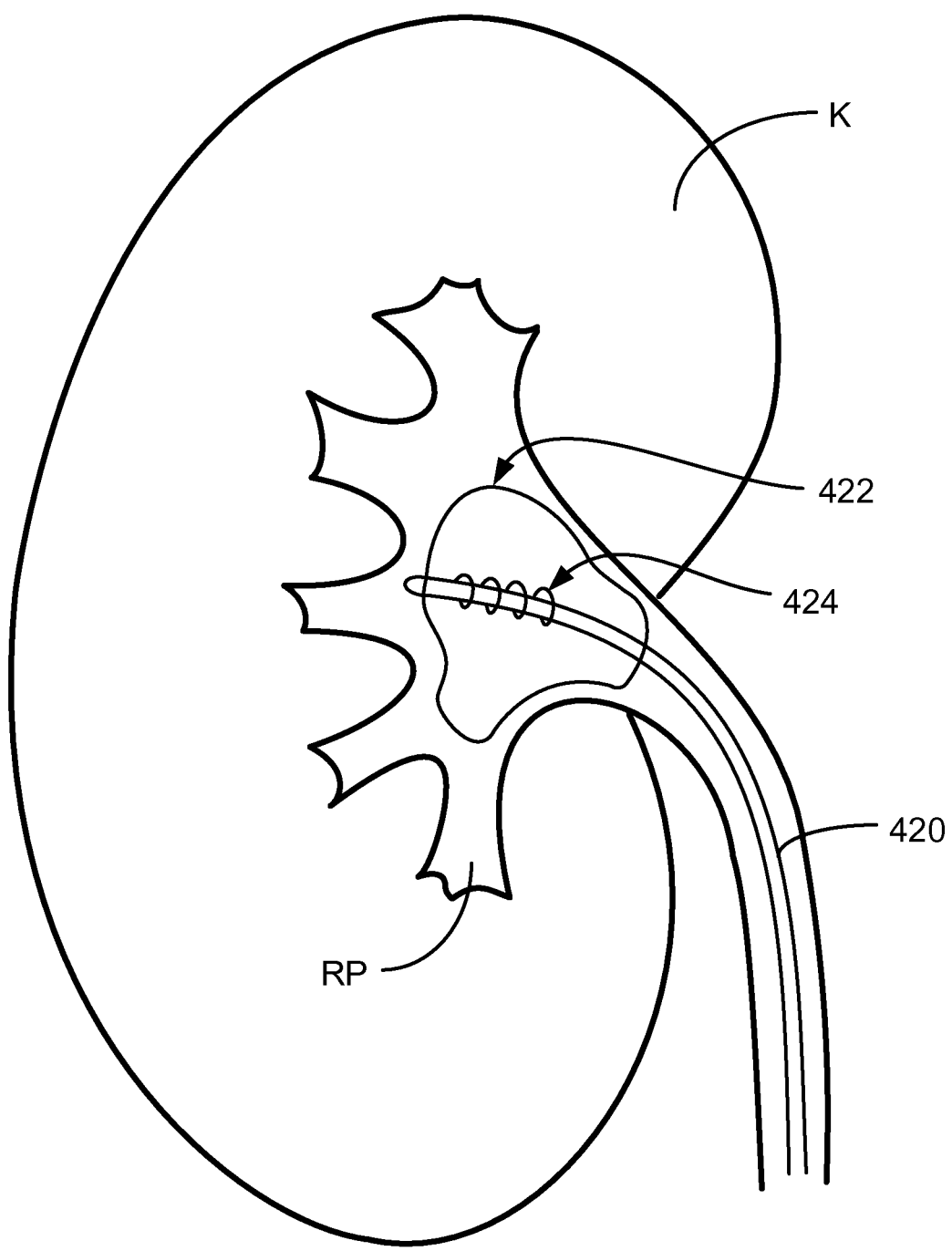
FIG. 43 shows a balloon catheter with heating coil.

As shown a FIG. 43, a catheter 420 carries a compliant or semi-compliant balloon 422 is deployable in the renal pelvis RP. The balloon 422 is inflated with saline or other liquid. The balloon is sufficiently compliant to conform to the anatomy of the renal pelvis to maximize wall contact. A resistive heating coil 424 made from a suitably resistive material, such as Nichrome®, is located inside the balloon. The coil heats the liquid to 60° C., and the balloon is maintained in place for a suitable time period against the wall of the renal pelvis to achieve the desired nerve ablation. Thermocouples located on the catheter and on the coil and inside the balloon can be used to regulate temperature. Alternatively, the liquid can be heated outside the catheter and pumped through the catheter/balloon assembly.

Figure 44A:
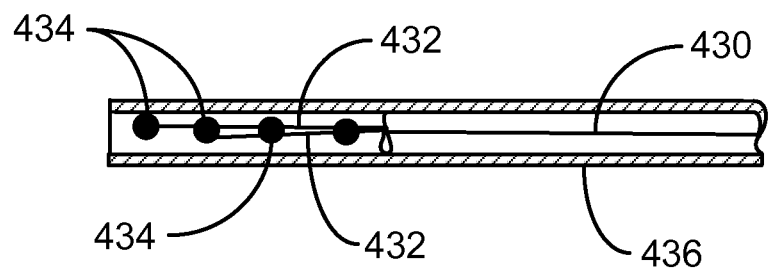
FIGS. 44A and 44B show a bifurcated superelastic alloy wire with ball electrodes.
Figure 44B:
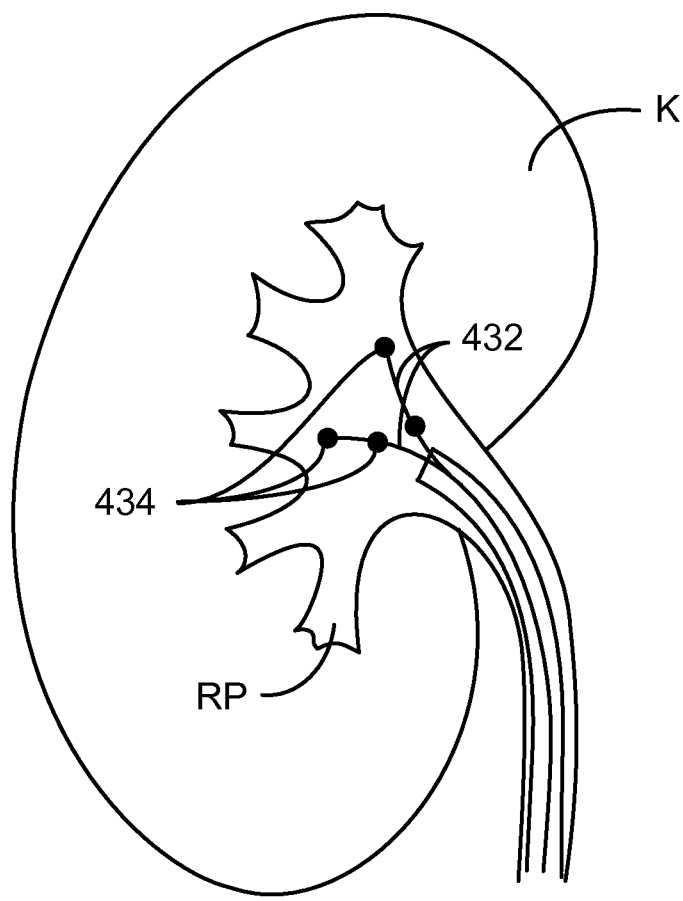

As shown in FIGS. 44A and 44B, a Nitinol® or other superelastic alloy wire 430 is bifurcated into branches 432 its distal end. Ball electrodes 434 are secured to each branch at alternating locations so that the branches can be collapsed within the lumen of a delivery sheath or catheter 436 as shown in FIG. 44A. The branches carrying the electrodes can be deployed out of the catheter and into the renal pelvis RP. The branches are biased apart to achieve spacing of the ball electrodes. RF energy is applied through the wire to the ball electrodes and discrete lesions are formed on the tissue wall. A vacuum can be applied to embed the ball electrodes into the tissue surface.

Figure 22:
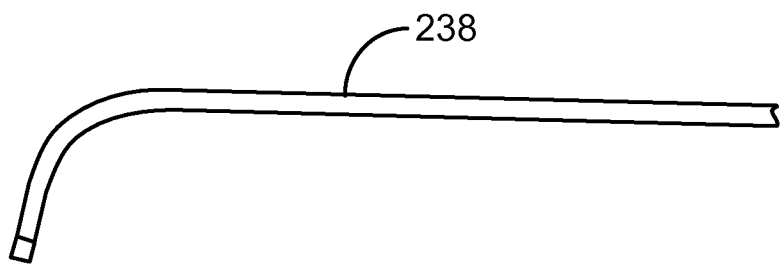
Figure 23:
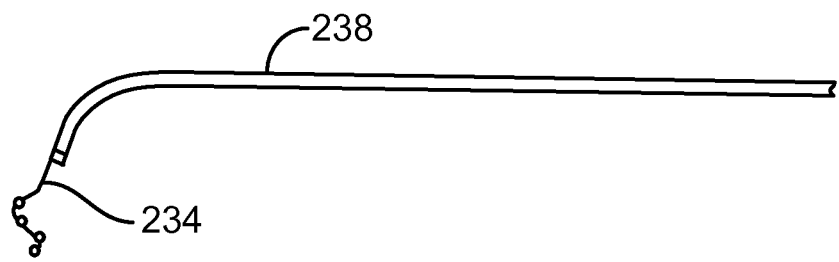
Figure 45:
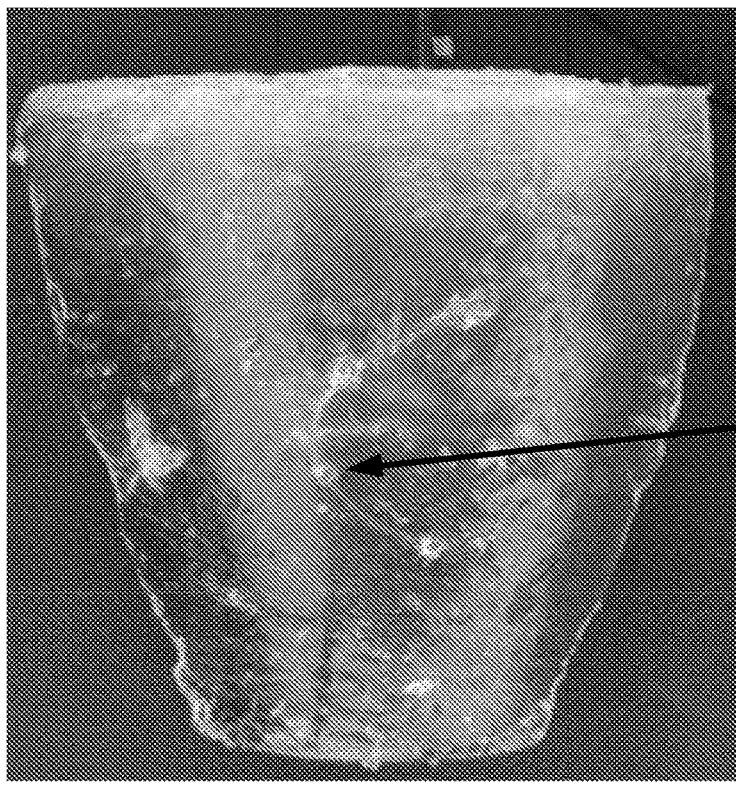
FIG. 45 shows a ball electrode device in temperature sensitive gel.
Figure 46:
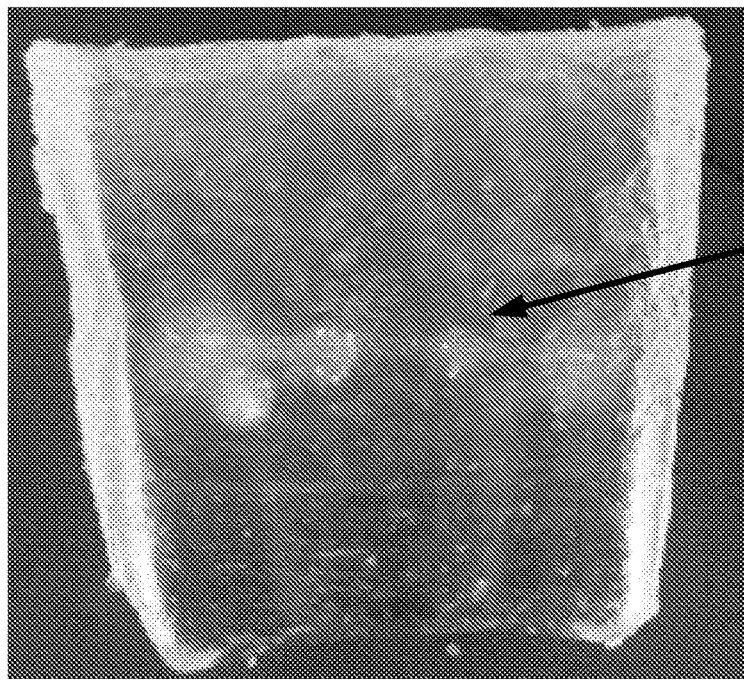
FIG. 46 shows a white clouding of the gel where the temperature was increased over 50 C.° from the device.

Applying RF or other heating means to the renal pelvis requires a balance of time and temperature. Too much energy will damage function of the renal pelvis. Not enough energy will prevent effective renal denervation. Experimentation has shown that a temperature in the range from 55° C. to 65° C., preferably 60° C. applied for a time in the range from 1 minute to 3 minutes, preferably 2 minutes, is optimal to achieve ablation of nerves surrounding the renal pelvis and in some cases the ureter. As shown in FIG. 45, ball electrodes are inserted into a gel phantom that mimics tissue electrical and thermal characteristics. The gel changes to a white color when the temperature is brought above 50° C. as shown in FIG. 22.

Many of the above-described device designs dilate, stretch, or otherwise tension the wall of the renal pelvis during the application of energy, the mechanical treatment of the renal pelvic wall, or substance delivery. This stretching is advantageous as it thins the tissue wall bringing the nerves closer to the treatment elements, particularly for the delivery of RF current.

What is claimed is:

1. A method for delivering energy to a renal pelvis of a human subject, the method comprising:
    inserting a sheath through a urinary tract of the human subject such that a distal opening of the sheath is disposed within a renal pelvis of the subject;
    providing a superelastic wire disposed within the sheath and including a distal region that has a pre-set shape and includes a plurality of discrete electrode elements, wherein the sheath constrains the distal region of the wire from expanding to the pre-set shape and wherein the superelastic wire does not include an internal cooling conduit;
    advancing the wire through the sheath distal opening such that the wire expands towards the pre-set shape within the renal pelvis;
    applying a vacuum through the sheath to at least partially evacuate the renal pelvis, thereby drawing two opposing wall portions of the renal pelvis inwards and compressing the expanded distal region of the wire, such that the opposing renal pelvic wall portions each intimately engage at least one of the discrete electrode elements; and
    while the renal pelvic wall portions are in intimate engagement with two or more of the plurality of electrode elements, applying radiofrequency (RF) energy through the plurality of discrete electrode elements to create, at locations corresponding to the renal pelvic wall engagement with the electrode elements, a plurality of discrete lesions extending the renal pelvic wall to ablate afferent nerves disposed within the wall of the renal pelvis.

2. The method of claim 1, wherein each of the plurality of discrete electrode elements is an RF electrode and applying energy comprises applying RF energy from an RF generator.

3. The method of claim 1, wherein each of the plurality of discrete lesions created by applying energy to the renal pelvic wall extends into the renal pelvic wall through a depth of 0.5 mm to 1.2 mm.

4. The method of claim 1, wherein step of at least partially evacuating removes fluid from the renal pelvis.

5. The method of claim 1, wherein the wire is monofilament or braided.

6. The method of claim 1, wherein the renal pelvic wall portions remain in intimate engagement with the electrodes during an entire period during which RF energy is applied.

* * * * *